United States Patent
Appella et al.

(10) Patent No.: US 10,457,978 B2
(45) Date of Patent: Oct. 29, 2019

(54) CYCLOPENTANE-PEPTIDE NUCLEIC ACIDS FOR QUALITATIVE AND QUANTITATIVE DETECTION OF NUCLEIC ACIDS

(71) Applicant: THE UNITED STATES OF AMERICA, AS REPRESENTED BY THE SECRETARY, DEPT. OF HEALTH AND HUMAN SERVICES, Bethesda, MD (US)

(72) Inventors: Daniel H. Appella, Rockville, MD (US); Christopher Micklitsch, Gaithersburg, MD (US); Bereket Yemane, Bridgewater, NJ (US); Chao Zhao, Rockville, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 103 days.

(21) Appl. No.: 14/421,732

(22) PCT Filed: Aug. 16, 2013

(86) PCT No.: PCT/US2013/055252
§ 371 (c)(1),
(2) Date: Feb. 13, 2015

(87) PCT Pub. No.: WO2014/028793
PCT Pub. Date: Feb. 20, 2014

(65) Prior Publication Data
US 2015/0218617 A1    Aug. 6, 2015

Related U.S. Application Data

(60) Provisional application No. 61/684,354, filed on Aug. 17, 2012.

(51) Int. Cl.
| | | |
|---|---|---|
| C12Q 1/70 | (2006.01) | |
| C12Q 1/682 | (2018.01) | |
| C12Q 1/6825 | (2018.01) | |

(52) U.S. Cl.
CPC .......... *C12Q 1/682* (2013.01); *C12Q 1/6825* (2013.01); *C12Q 1/703* (2013.01); *C12Q 2525/107* (2013.01); *C12Q 2525/113* (2013.01); *C12Q 2525/119* (2013.01); *C12Q 2563/131* (2013.01)

(58) Field of Classification Search
None
See application file for complete search history.

(56) References Cited

U.S. PATENT DOCUMENTS

| | | | | |
|---|---|---|---|---|
| 6,361,951 | B1* | 3/2002 | Thorp | B82Y 15/00 |
| | | | | 435/6.13 |
| 6,660,845 | B1* | 12/2003 | Gall | A61K 31/519 |
| | | | | 435/6.11 |
| 2002/0012921 | A1* | 1/2002 | Stanton, Jr. | G06F 19/18 |
| | | | | 435/6.16 |
| 2004/0006203 | A1* | 1/2004 | Maier | C07H 21/00 |
| | | | | 530/333 |
| 2006/0057595 | A1* | 3/2006 | Lao | C12Q 1/6851 |
| | | | | 435/6.12 |
| 2006/0252081 | A1* | 11/2006 | Hyldig-Nielsen | C12Q 1/6816 |
| | | | | 435/5 |
| 2007/0212704 | A1* | 9/2007 | Dong | C12P 19/34 |
| | | | | 435/6.12 |
| 2008/0160532 | A1* | 7/2008 | Shah | C12Q 1/6893 |
| | | | | 435/6.15 |
| 2010/0021971 | A1 | 1/2010 | Chen et al. | |
| 2010/0120031 | A1* | 5/2010 | Appella | C07C 271/24 |
| | | | | 435/6.1 |
| 2010/0260745 | A1* | 10/2010 | Zhou | B82Y 15/00 |
| | | | | 424/130.1 |
| 2010/0261159 | A1* | 10/2010 | Hess | B01J 19/0046 |
| | | | | 435/6.14 |
| 2015/0197571 | A1* | 7/2015 | Freeman | G01N 33/57492 |
| | | | | 424/136.1 |

OTHER PUBLICATIONS

"How many species of bacteria are there?" (WiseGeek.com, accessed Jan. 21, 2014).*
To "How many species of bacteria are there" (Wisegeek.com; accessed Jan. 21, 2014).*
"List of sequenced bacterial genomes" (Wikipedia.com; accessed Jan. 24, 2014).*
"Pathogen," (Wikipedia.com, accessed Apr. 27, 2017).*
"Subtypes of HIV", Wikipedia.com; accessed Oct. 24, 2018. (Year: 2018).*
Taylor et al., "The Challenge of HIV-1 Subtype Divesity", N Engl J Med., Apr. 10, 2008; 358(15): 1590-1602. (Year: 2008).*
Kozal et al., "Extensive polymorphisms observed in HIV-1 Glade B protease gene using high-density oligonucleotide arrays", Nature, vol. 2, No. 7,Jul. 1996, pp. 753-759. (Year: 1996).*

(Continued)

*Primary Examiner* — Bradley L. Sisson
(74) *Attorney, Agent, or Firm* — Leydig, Voit & Mayer, Ltd.

(57) ABSTRACT

The invention concerns methods for detecting a nucleic acid of interest in a solution comprising (a) contacting a solution suspected of containing the nucleic acid of interest with a PNA capture probe and a PNA reporter probe; wherein (i) the PNA capture probe comprises at least two trans-cyclopentanes; (ii) the PNA reporter probe comprises at least six biotin groups; (iii) the PNA capture probe bound to a surface; and (iv) the PNA capture probe and the PNA reporter probe each comprise a nucleobase sequence that is complementary to different non-overlapping portions of the nucleic acid of interest; (b) detecting the presence of the PNA capture probe and the PNA reporter probe bound to the surface; wherein the nucleic acid of interest is detected when 1-1000 molecules of the nucleic acid of interest are present in the solution being tested.

8 Claims, 44 Drawing Sheets
Specification includes a Sequence Listing.

(56) References Cited

OTHER PUBLICATIONS

International Search Report, Application No. PCT/US2013/055252, dated Dec. 16, 2013, 5 pages.
Written Opinion of the International Searching Authority, Application No. PCT/US2013/055252, dated Dec. 16, 2013, 7 pages.
International Preliminary Report on Patentability, Application No. PCT/US2013/055252, dated Feb. 26, 2015, 6 pages.
Micklitsch et al., "Cyclopentane-peptide nucleic acids for qualitive, quantitative, and repetitive detection of nucleic acids" *Analytical Chemistry*, 85, 251-257 (Dec. 10, 2012) including supporting information.
Pokorski et al., "Cyclopentane-modified PNA improves the sensitivity of nanoparticle-based scanometric DNA detection" *Chemical Communications, Royal Society of Chemistry*. GB, 16, 2101-2103 (Apr. 2005),
Zhang et al., "Colorimetric detection of anthrax DNA with a peptide nucleic acid sandwich-hybridization assay" *Journal of the American Chemical Society ACS* Publications, 129(27) 8424-8425 (Jan. 2007).

\* cited by examiner

| FIG. 6A | FIG. 6B | FIG. 6C | FIG. 6D | FIG. 6F | FIG. 6H |
|---------|---------|---------|---------|---------|---------|
|         |         |         | FIG. 6E | FIG. 6G | FIG. 6I |

Reporter Probe 6 (RP6)

Chemical Formula: $C_{666}H_{1079}N_{193}O_{198}S_{20}$
Exact Mass: 15588.47
Molecular Weight: 15599.17

HIV-1 gag DNA: 5'-TTC TGC AGC TTC CTC ATT GAT GGT CTC-3'
HIV-1 gag RNA: 5'-UUC UGC AGC UUC CUC AUU GAU GGU CUC-3'

SEQUENCE LISTING

```
<160> NUMBER OF SEQ ID NOS: 11

<210> SEQ ID NO 1
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (8)..(8)
<223> OTHER INFORMATION: (S,S)-transcyclopentane modified thymine

<400> SEQUENCE: 1
atccttatca atatt                                                      15

<210> SEQ ID NO 2
<211> LENGTH: 15
```

```
<212> TYPE: DNA
<213> ORGANISM: Artificial Sequence
<220> FEATURE:
<223> OTHER INFORMATION: Synthetic

<400> SEQUENCE: 2
atccttatca atatt                                                    15

<210> SEQ ID NO 3
<211> LENGTH: 12
<212> TYPE: DNA
<213> ORGANISM: Artificial Sequence
<220> FEATURE:
<223> OTHER INFORMATION: Synthetic

<400> SEQUENCE: 3
taacaataat cc                                                       12

<210> SEQ ID NO 4
<211> LENGTH: 27
<212> TYPE: DNA
<213> ORGANISM: Bacillus anthracis

<400> SEQUENCE: 4
ggattattgt taaatattga taaggat                                       27

<210> SEQ ID NO 5
<211> LENGTH: 50
<212> TYPE: DNA
<213> ORGANISM: Artificial Sequence
<220> FEATURE:
<223> OTHER INFORMATION: Synthetic

<400> SEQUENCE: 5
gctgaaatat aggattattg ttaaatattg ataaggatgt aatgataata              50

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
tgcagtctgt tacaatgacc tact                                          24

<210> SEQ ID NO 7
<211> LENGTH: 50
<212> TYPE: DNA
<213> ORGANISM: Artificial Sequence
<220> FEATURE:
<223> OTHER INFORMATION: Synthetic

<400> SEQUENCE: 7
gctgaaatat aaagataaat aggtgtcaat tgtagaacgt aatgataata              50

<210> SEQ ID NO 8
<211> LENGTH: 27
<212> TYPE: DNA
<213> ORGANISM: Human immunodeficiency virus type 1

<400> SEQUENCE: 8
ttctgcagct tcctcattga tggtctc                                       27

<210> SEQ ID NO 9
```

```
<211> LENGTH: 27
<212> TYPE: RNA
<213> ORGANISM: Human immunodeficiency virus type 1

<400> SEQUENCE: 9
uucugcagcu uccucauuga uggucuc                                         27

<210> SEQ ID NO 10
<211> LENGTH: 15
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(15)
<223> OTHER INFORMATION: residues 1 through 15 are linked by peptide
      bonds
<220> FEATURE:
<221> NAME/KEY: modified_base
<222> LOCATION: (4)..(4)
<223> OTHER INFORMATION: (S,S)-transcyclopentane modified adenine
<220> FEATURE:
<221> NAME/KEY: modified_base
<222> LOCATION: (8)..(8)
<223> OTHER INFORMATION: (S,S)-transcyclopentane modified cytosine
<220> FEATURE:
<221> NAME/KEY: modified_base
<222> LOCATION: (10)..(10)
<223> OTHER INFORMATION: (S,S)-transcyclopentane modified adenine
<220> FEATURE:
<221> NAME/KEY: modified_base
<222> LOCATION: (12)..(12)
<223> OTHER INFORMATION: S,S)-transcyclopentane modified uracil

<400> SEQUENCE: 10
gagaccatca atgag                                                      15

<210> SEQ ID NO 11
<211> LENGTH: 12
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(12)
<223> OTHER INFORMATION: residues 1 through 12 are linked by peptide
      bonds

<400> SEQUENCE: 11
gaagctgcag aa                                                         12
```

CYCLOPENTANE-PEPTIDE NUCLEIC ACIDS FOR QUALITATIVE AND QUANTITATIVE DETECTION OF NUCLEIC ACIDS

CROSS REFERENCE TO RELATED APPLICATIONS

This application is a U.S. National Phase of International Patent Application No. PCT/US2013/055252, filed Aug. 16, 2013, which claims the benefit of U.S. Provisional Patent Application No. 61/684,354, filed on Aug. 17, 2012, the disclosures of which are incorporated herein by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 3,115 Byte ASCII (Text) file named "719470ReplacementSequenceListing" dated Jan. 28, 2019.

TECHNICAL FIELD

The invention relates to cyclopentane-peptide nucleic acids and their use in qualitative and quantitative detection of nucleic acids.

BACKGROUND

PNA is a DNA mimic, in which the entire negatively-charged sugar phosphate backbone is replaced with a neutral one consisting of repeated N-(2-aminoethyl) glycine units linked by peptide bonds. It is stable chemically and biologically.

Nucleic acid testing is highly specific and often provides definitive identification of a disease or pathogen. Methods to detect nucleic acid sequences are dominated by PCR, but applying PCR-based techniques outside of a modern laboratory is challenging. Samples collected in the field, for instance, typically contain inhibitors of the polymerases used in PCR amplification. These inhibitors can be naturally occurring (such as humic acids, urea, heme, Ca2+, proteinases, and/or polysaccharides) or come from items used to collect the samples (namely glove powder, NaCl, KCl, EDTA, SDS, and phenol). These inhibitors can be difficult to remove from samples in the field. While there are other non-PCR-based detection platforms for nucleic acid analysis, they are similarly limited to a laboratory environment.

SUMMARY

To overcome the problems of stability to outside contamination, we developed peptide nucleic acid (PNA) probes for use in a diagnostic system that does not rely on PCR. PNA binds to DNA using Watson-Crick base pairing, and it binds with greater stability and selectivity compared to a complementary DNA sequence. In addition, PNAs are resistant to enzymatic proteolysis because of the aminoethylglycyl (aeg) backbone. While aegPNA is widely available and has been incorporated into some detection platforms, the recent emergence of chemically-modified PNA derivatives with enhanced binding properties provides many more opportunities for developing a diagnostic device. In theory, PNA-based nucleic acid probes can be coupled with emerging technological platforms for detection to afford a device that may be used outside of laboratory settings. The use of PNAs for nucleic acid testing should provide a high degree of stability to any diagnostic device and PNA probes could in principle be used to detect many different pathogenic agents and diseases (such as HIV, plague, influenza, or botulism). In our own work, we have found that incorporation of a cyclopentane ring into the backbone of aegPNA improves binding to complementary DNA and improves sequence specificity. Other PNA analogs are similarly available, but there has been no rigorous evaluation of any modified PNAs to determine whether they can indeed be incorporated into a diagnostic device. The present application, in some aspects, focuses on cyclopentane-PNA probes for detection of anthrax DNA and HIV RNA, with a focus on evaluating the ability of PNA probes to provide both qualitative and quantitative detection of nucleic acids. Establishing these parameters is important to demonstrate that PNA possesses properties suitable for use in detection platforms. Herein, we present details of sandwich hybridization assays using PNA probes (FIG. 1) along with the in depth evaluation of qualitative vs quantitative regions for nucleic acid detection. Ultimately, this work validates the use of PNA probes for incorporation into diagnostic devices for nucleic acid testing and should incentivize incorporation of PNA into emerging technologies for detection.

One of the great challenges in human immunodeficiency virus (HIV) diagnosis and prevention today is to develop technologies to early and direct detection of HIV-1 nucleic acid sequences in patient tissue or blood samples. Enzymatic amplification of conserved sequences of the HIV-1 genome by PCR has been the subject of a large number of studies. However, the direct biochemical test used for PCR-based molecular diagnosis of HIV-1 infection is usually time consuming, is not quantitative and requires molecular biology facilities. So, direct detection methods that eliminate the requirement for a PCR step could afford faster and simpler devices that can be used outside of a laboratory.

Presented herein is a convenient, universal, colorimetric, nucleic acid-responsive detection system that uses two short peptide nucleic acids (PNAs) is demonstrated for the ultra-high sensitive detection of HIV-1 nucleic acids on a 96-well plate based on the sandwich-hybridization strategy. This protocol eliminates the requirement for a PCR step, and greatly improves the detection devices by using PNA probes instead of traditional DNAs for its outstanding properties. Furthermore, the design of a 4-cyclopentane modified surface probe and a 20-biotin containing reporter probe impart extraordinarily high sensitivity. This sandwich-hybridization assay is convenient, universal and colorimetric with a qualitative detection limit of 1 molecule for both of HIV-1 gag DNA and RNA, and a quantitative detection limit of 3 molecules for HIV-1 gag DNA, 2 molecules for HIV-1 gag RNA. For the HIV-1 real samples, the quantitative detection limit is around 50 copies, and the qualitative detection limit can down to 1 copy. These properties should make this device suitable for early detection of HIV virus among other uses.

In some aspects, the invention concerns methods for detecting a nucleic acid of interest in a solution, the method comprising (a) contacting a solution suspected of containing the nucleic acid of interest with a PNA capture probe and a PNA reporter probe; wherein
  (i) the PNA capture probe comprises at least two trans-cyclopentanes;
  (ii) the PNA reporter probe comprises at least six biotin groups;

(iii) the PNA capture probe bound to a surface; and
(iv) the PNA capture probe and the PNA reporter probe each comprise a nucleobase sequence that is complementary to different non-overlapping portions of the nucleic acid of interest;
(b) detecting the presence of the PNA capture probe and the PNA reporter probe bound to the surface;
wherein the nucleic acid of interest is detected when 1-1000 molecules of the nucleic acid of interest are present in the solution being tested.

In some embodiments, the surface is visually observed to detect the appearance of a detectable signal from the reporter probe. In certain embodiments, the detecting is performed visually by an observer. The surface may be washed prior to determining the presence of the reporter probe.

In some methods, 40-600 molecules of the nucleic acid of interest are present in the solution, and the method further comprises quantifying the number of nucleic acid molecules of interest present in the solution wherein the amount of signal detected from the PNA reporter probe is proportional to the number of nucleic acid molecules of interest.

In certain methods, the PNA reporter probe biotin groups are bound to at least one of avidin-conjugate or streptavidin-conjugate.

Certain methods allow for the nucleic acid of interest is detected when 1-40 molecules of the nucleic acid are present in the solution being tested.

The methods of the invention are versatile and can be used to detect a wide variety of nucleic acids. These nucleic acids of interest include a nucleic acid present in anthrax, avian flu, severe acute respiratory syndrome (SARS), tuberculosis (TB), human papilloma virus (HPV), or human immunodeficiency virus (HIV), carbapenem-resistant *Klebsiella pneumoniae*, or multidrug resistant/extensively drug resistant (MDR/XDR) tuberculosis. In some preferred embodiments, the nucleic acid of interest is HIV-1 RNA. In certain embodiments, the nucleic acid of interest is HIV gag.

In some embodiments, determining the presence of the PNA reporter probe on the surface is performed by visual inspection for color.

In certain embodiments, the PNA reporter probe biotin groups are bound to a horseradish peroxidase-avidin or horseradish peroxidase-streptavidin conjugate. In some methods, the PNA reporter probe comprises 6-30 biotin groups.

Some methods of the invention utilize a PNA capture probe that comprises at least two trans-cyclopentanes. Certain PNA capture probes comprise at least three trans-cyclopentanes.

Certain preferred method relate to a method where the nucleic acid of interest is detected in a patient at a quantifiable level of less than 50 copies per ml of biological sample, and the HIV status of the patient is then categorized as dormant or in remission. In some methods, the nucleic acid of interest is detected in a patient at a quantifiable level of greater than 50 copies per mL of biological sample, and the HIV status of the patient should be evaluated for possible activity or relapse.

In some preferred embodiments, the surface to which the PNA capture probe is bound is a plastic support, resin, gel, paper or cellulose.

In other aspects, the invention concerns kits for detecting nucleic acid. Some kits are designed for detecting a 1-1000 molecules of a nucleic acid of interest present in a solution. Certain kits comprise (a) a PNA capture probe comprising at least two trans-cyclopentanes; the PNA capture probe being bound to a surface; (b) a PNA reporter probe comprising at least 6 biotin groups; and (c) at least one of avidin-conjugate and streptavidin-conjugate; wherein the PNA capture probe and the PNA reporter probe each comprise a nucleobase sequence that is complementary to different non-overlapping portions of the nucleic acid of interest.

In some kits, the avidin-conjugate comprises horseradish peroxidase-avidin. In certain kits, the streptavidin-conjugate comprises polyhorseradish peroxidase-streptavidin. In some kits, the avidin-conjugate comprises avidin-conjugated gold nanoparticles.

In some embodiments, the PNA reporter probe comprises 6-30 biotin groups. In certain kits, the PNA capture probe comprises at least two trans-cyclopentanes.

Kits may further comprise a wash solution for use at least once after a binding step.

While any suitable material may be utilized, in some kits the surface to which the PNA capture probe is bound is a plastic support, resin, gel, paper or cellulose.

DETAILED DESCRIPTION OF ILLUSTRATIVE EMBODIMENTS

Nucleic acid-based probes for genomic detection are attractive tools for biomedical research and its application for disease detection. However, replacing DNA probes with PNAs, can significantly improve detection devices for its outstanding properties: complete resistance to degradation by enzymes; increased sequence specificity to complementary DNA; higher stability when bound with complementary DNA. Cyclopentane groups can efficiently improve the melting temperature and sequence specificity of PNA-DNA duplexes. Addition of one or more cyclopentane groups into a PNA sequence improves the melting temperature to complementary DNA by about 5° C. per cyclopentane, regardless of which base is used.

The invention concerns the development of chemically modified peptide nucleic acids (PNAs) as probes for qualitative and quantitative detection of DNA. The remarkable stability of PNAs toward enzymatic degradation makes this class of molecules ideal to develop as part of a diagnostic device that can be used outside of a laboratory setting. Using an enzyme-linked reporter assay, we demonstrate that excellent levels of detection and accuracy for anthrax DNA and for HIV RNA can be achieved using PNA probes with suitable chemical components designed into the probe. The results presented herein are the first detailed examination of the qualitative and quantitative properties of chemically-modified PNA for nucleic acid detection and provides a platform for studying and optimizing PNA probes prior to incorporation into new technological platforms.

Results & Discussion:

Detection of Pag Anthrax DNA Via Sandwich Hybridization

Detection assays ideally confirm the presence of an agent and reveal the amount of the agent that is present. One way to identify the genetic material of biological agents uses Watson-Crick base pairing of a target DNA with two synthetic, nucleic acid probes to form a sandwich-hybridized complex that can be detected by one of several methods known to those skilled in the art. In our work, the nucleic acid probes (Table 1) are peptide nucleic acids (PNAs).

TABLE 1

PNA Probes

| Probe | Sequence |
| --- | --- |
| SP1 | $H_2N$-(mPEG)$_5$-ATCCTTATcypCAATATT-CONH$_2$ (SEQ. ID. NO. 1) |
| SP2 | Ac-(mPEG)$_2$-ATCCTTATCAATATT-Lys(mPEG-Cys-NH$_2$)-CONH$_2$ (SEQ. ID. NO. 2) |
| SP3 | $H_2N$-(mPEG)2-ATCCTTATcypCAATATT-Lys(mPEG-SPDP)-CONH$_2$ (SEQ. ID. NO. 1) |
| RP1 | Ac-TAACAATAATCC-mPEG-2-[Lys(mPEG3-BT)]2-[Lys(mPEG-BT)]2-Lys(NH2)-CONH$_2$ (SEQ. ID. NO. 3) |
| RP2 | Mal-mPEG-TAACAATAATCC-Lys(mPEG-Ac)-CONH$_2$ (SEQ. ID. NO. 3) |
| RP3 | Mal-mPEG-TAACAATAATCC-mPEG-2-[Lys(mPEG3-BT)]2-[Lys(mPEG-BT)]2-Lys(NH2)-CONH$_2$ (SEQ. ID. NO. 3) |

Abbreviations: mPEG: 8-amino-3,6-dioctanoic acid; Mal: (N-maleimidopropionamido)-tetraeythyleneglycol; SPDP: 3-(2-pyridyldithio)-propionic acid; Tcyp: (S, S)-

Figure 1:
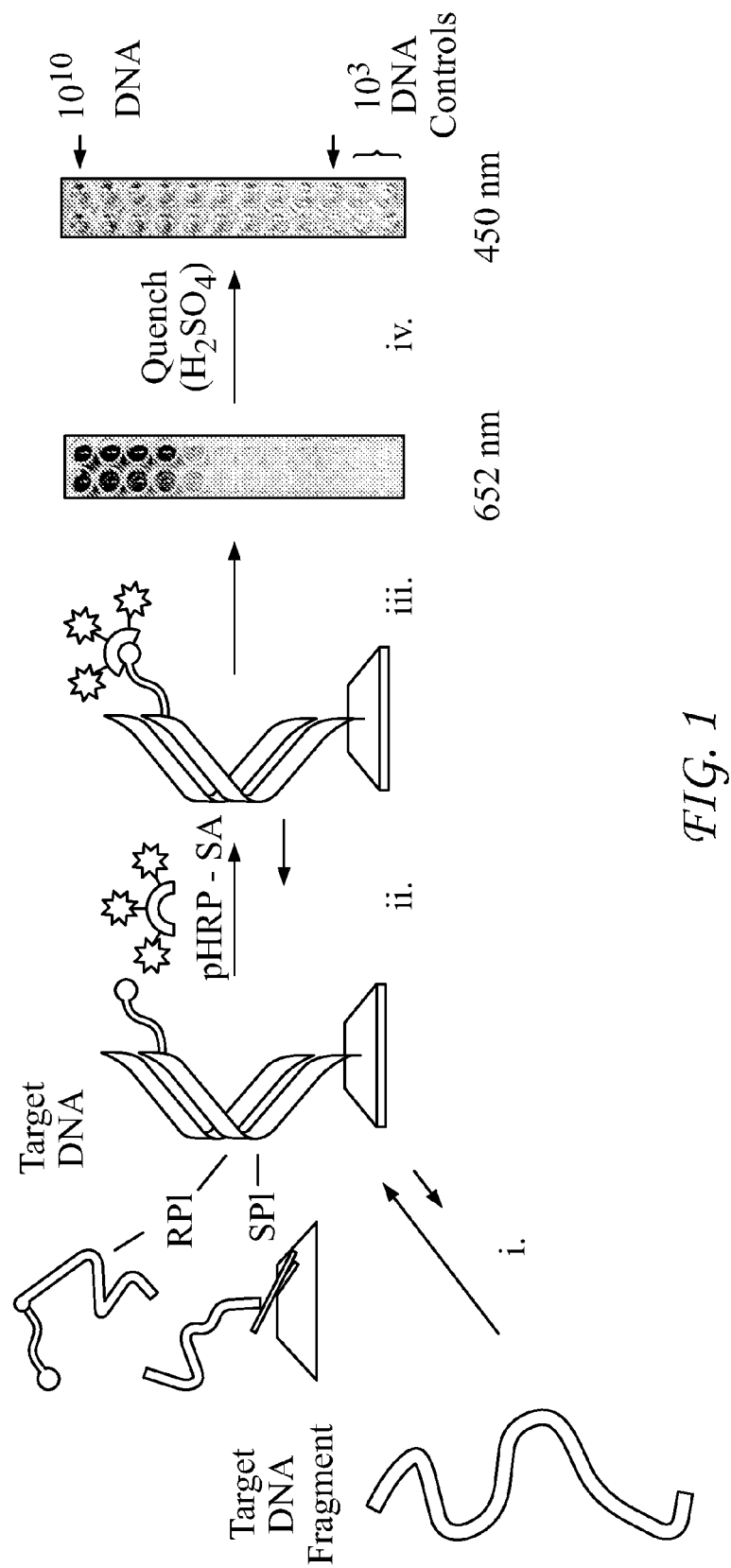
FIG. 1 presents schemes for the detection method using PNA probes. Non-covalent sandwich: PNA probes RP1 and SP1 recognize a 27-base sequence of anthrax DNA or HIV RNA and form a three-component, non-covalent complex on a plastic surface. Probe RP1 has six to thirty biotins on the C-terminal. If the target DNA or RNA is present and the complex forms, a color can be developed by introducing a polyhorseradish peroxidase+streptavidin conjugate followed by a solution of tetramethylbenzidine and peroxide. Enzymatic oxidation initially produces a blue color at 652 nm, quenching the enzyme with sulfuric acid produces a yellow color at 450 nm.

The PNA probes constitute two halves of a hybridization sandwich (FIG. 1). The N-terminus of the 15-bp surface probe (SP) is chemically immobilized to the wells of a multiwell plate comprising a polystyrene surface having a surface-attached quinone moiety comprising a (poly)ethyleneglycol-linker-attached electrophilic moiety, wherein the electrophilic moiety is reactive with amino groups, while the 12-bp reporter probe (RP) has six biotins coupled to the C-terminus. A non-limiting example of a suitable multiwall plate is a "Nunc Immobilizer Amino™" 96-well plate, available from Thermo Fisher Scientific, Waltham, Mass. The two PNA probes were designed to hybridize to a 27-bp DNA sequence from the highly conserved pag-coding (PA) portion of the pX01 gene of *B. anthraces* (TS1, Table 2). The mPEG (8-amino-3,6-dioxaoctanoic acid) spacers in RP1 and RP3 were incorporated to provide sufficient spacing so that neighboring biotins would not interfere with binding to a poly-horseradish peroxidase-streptavidin conjugate (pHRP-SA). The six biotins provide multiple sites for pHRP-SA to bind to (i.e. label) the reporter probe to amplify signal resulting from DNA hybridization. In this study, SP1 and RP1 form non-covalent complexes with the target DNA while the other probes in Table 1 were designed to form cross-linked dimers upon binding to the DNA target (FIG. 1, vide infra).

TABLE 2

Nucleic Acid Targets

| Name | Nucleic Acid Type | Sequence |
|---|---|---|
| TS1 | DNA (27 bp) | 5'-GGA-TTA-TTG-TTA-AAT-ATT-GAT-AAG-GAT-3' (SEQ. ID. NO. 4) |
| TS2 | DNA (27 bp) (ds) | 5'-GGA-TTA-TTG-TTA-AAT-ATT-GAT-AAG-GAT-3'<br>3'-CCT-AAT-AAC-AAT-TTA-TAA-CTA-TTC-CTA-5'<br>(SEQ. ID. NO. 4) |
| TS3 | DNA (50 bp)<br><br>(ds) | 5'-GCTGAAATATAGGATTATTGTTAAATATTGATAAGGATGTAATGATAATA-3' (SEQ. ID. NO. 5)<br><br>3'-CGACT TTATATCCTAATAACAATTTATAACTATTCCTACATTACTATTAT-5' |
| SS1 | Control (24 bp) | 5'-TGC-AGT-CTG-TTA-CAA-TGA-CCT-ACT-3' (SEQ. ID. NO. 6) |

Abbreviations: bp: base pairs; ds: double-stranded. Underlined portions of sequences indicate target regions of PNA probes.

After DNA hybridization with the PNA probes and careful washing to remove nonspecifically bound agents, any biotin retained to the surface as a result of both PNAs hybridizing to DNA can be detected via labeling the biotins with pHRP-SA followed by addition of tetramethylbenzidine (TMB) and peroxide. When pHRP-SA is present, the enzyme uses peroxide to oxidize TMB, which gives a blue color (652 nm). Enzymatic oxidation is quenched with the addition of $H_2SO_4$, resulting in a yellow color (450 nm) that can also be quantified. To investigate the utility of this assay, we investigated the ranges of qualitative and quantitative detection by two methods: development of signal at 652 nm and signal values at 450 nm after quenching enzymatic oxidation. In addition, we investigated the response of the assay to multiple forms of DNA targets, including single-stranded (ss) and double-stranded (ds) DNA.

Figure 2A:
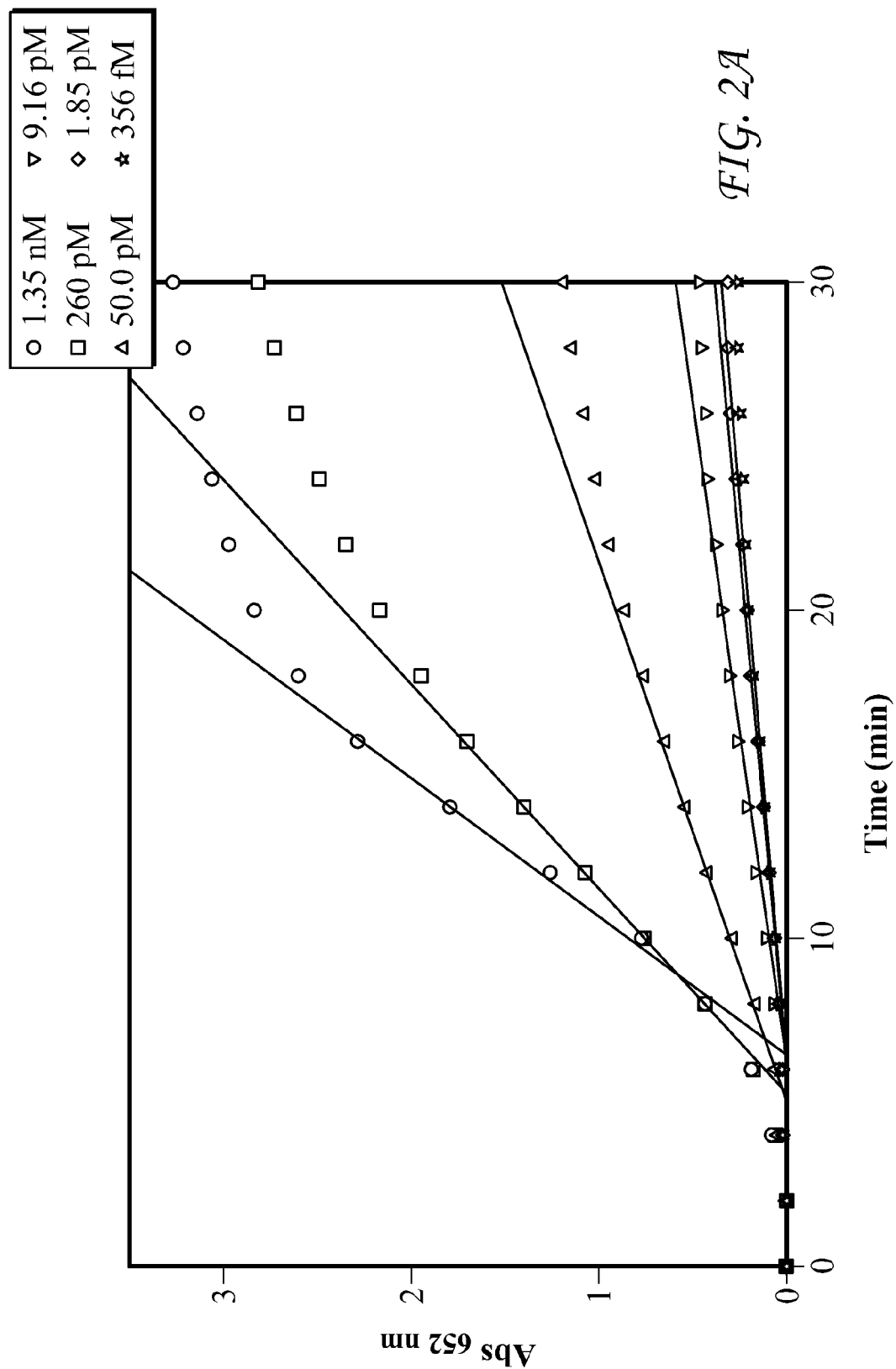
FIG. 2 presents data on detection of DNA using PNA probes SP1 and RP1. A. Absorbance data (652 nm) for detection of TS1 DNA over a range of concentrations and linear regression analyses of maximum velocities (VMax) for each concentration. B. Signal response plot (VMax vs. [DNA]) for each DNA in Table 2 and curve fits for each plot. C. Signal response plot (Absorbance at 450 nm vs. [TS1 DNA]) obtained after quenching of enzymatic oxidation with $H_2SO_4$.
Figure 2B:
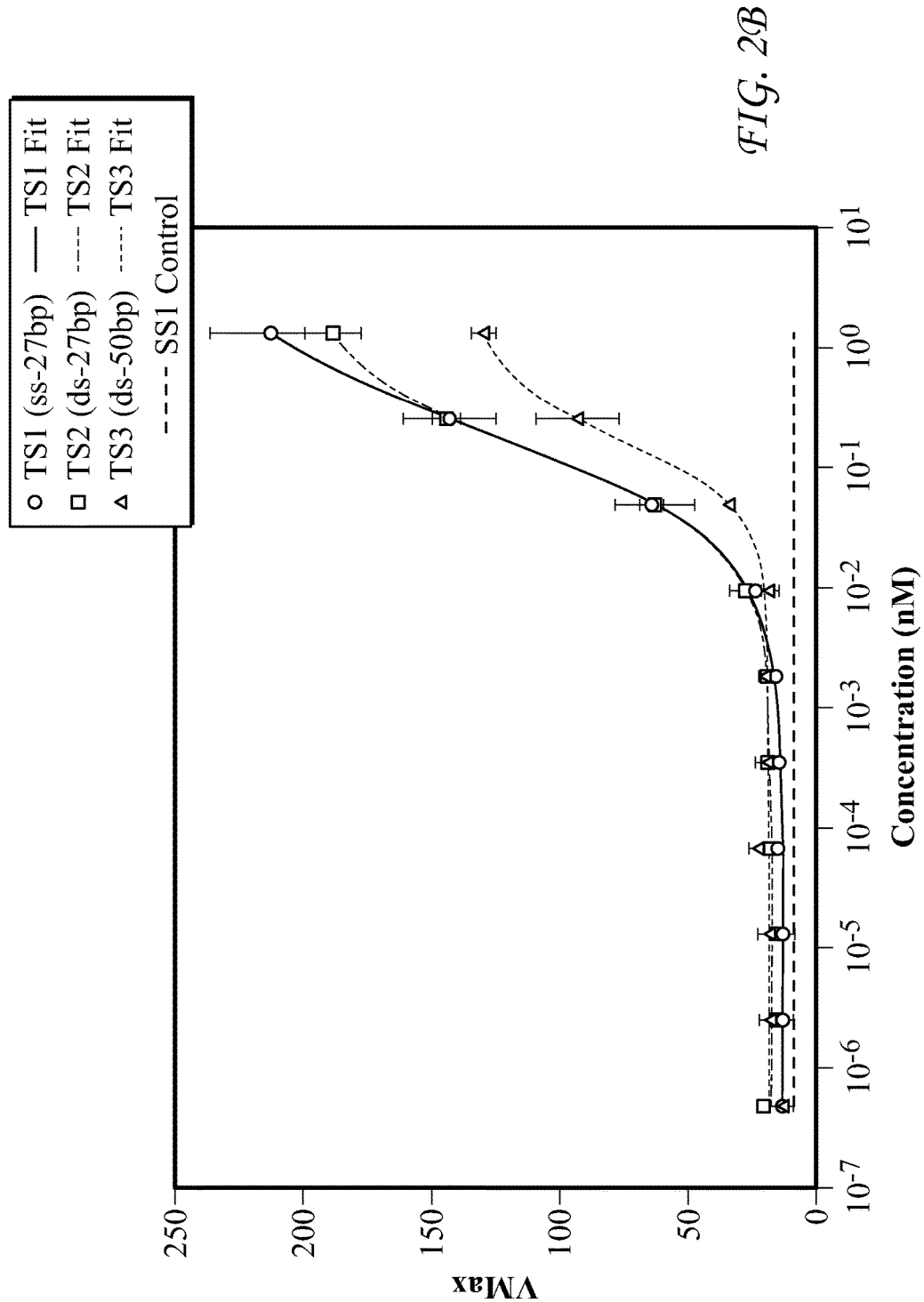
Figure 2C:
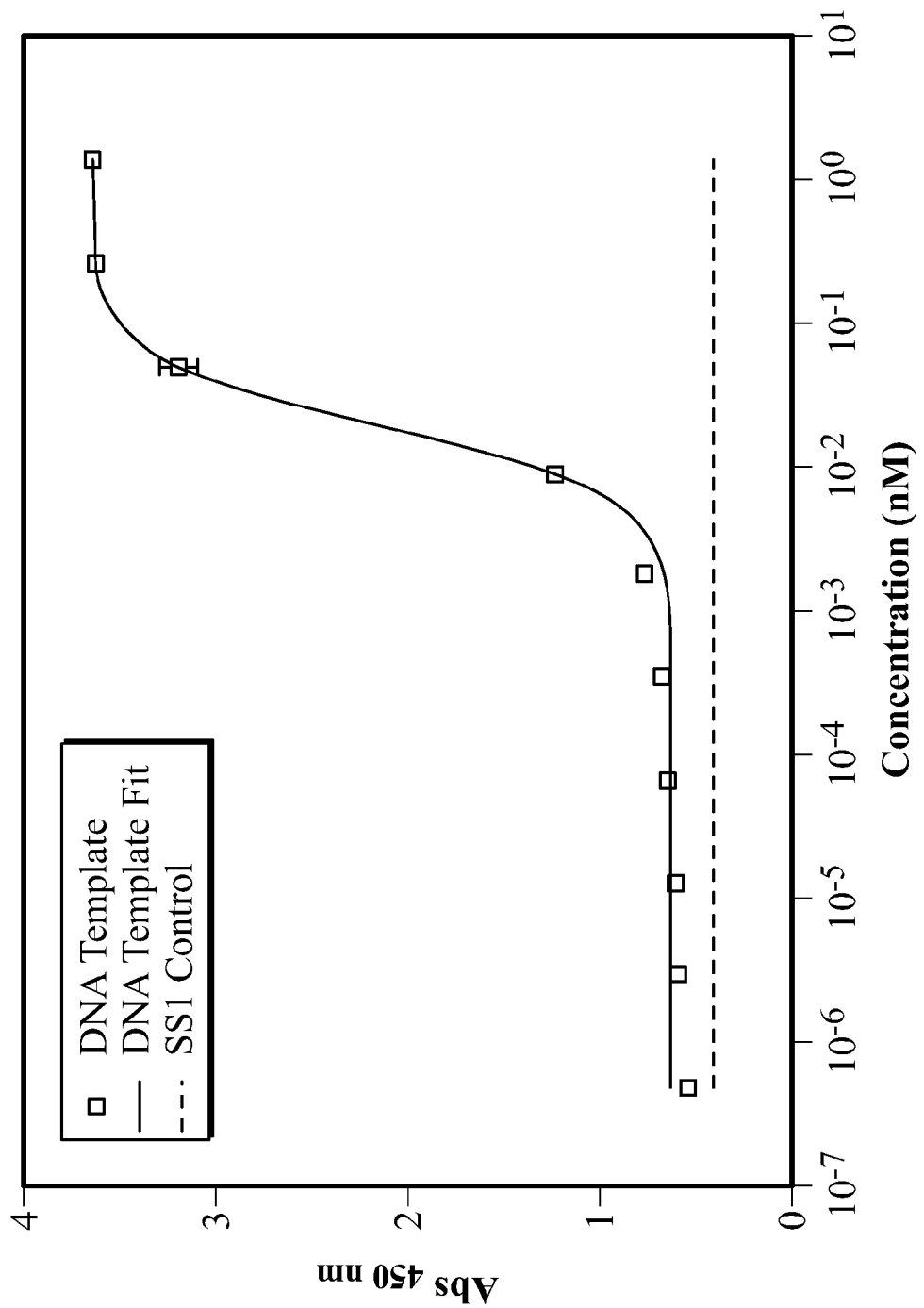

Development of signal at 652 nm results from the buildup of oxidized TMB that is catalyzed by HRP. The rate of TMB oxidation is proportional to the amount of enzyme bound to the reporter PNA, which is itself proportional to the amount of target DNA. Therefore, each concentration of DNA results in a different sigmoidal curve that reflects the amount of the surface bound pHRP-SA after hybridization of the PNA probes to the target DNA. After PNA hybridization to target DNA and labeling with pHRP-SA, a solution of TMB and peroxide was added and development of signal at 652 nm was monitored for 30 minutes with absorbance values collected every 120 seconds. A linear best-fit line was applied to the rate of growth of absorption data to determine the maximal velocity VMax (as defined in the software package SpectaMax™). The initiation and leveling-off phases of the absorption data were excluded from the fit. The slope of the line fit was assigned to VMax, and this value was calculated for each concentration. FIG. 2A shows the signal response detected by probes SP1 and RP1 for DNA TS1 over a concentration range of four-orders of magnitude. For data acquired at 652 nm, we consider a plot of VMax versus concentration of DNA to reflect the signal response of the assay (FIG. 2B). Similar analyses for each nucleic acid in Table 2 were performed, and the results are plotted together on FIG. 2B. The response curves were each fit to a 4-parameter logistic curve that reveals the qualitative and quantitative regions of the assay. In contrast to monitoring development of signal at 652 nm, the data obtained at 450 nm, which are obtained after quenching enzymatic oxidation with sulfuric acid, are single values of absorbance versus concentration of DNA. FIG. 2C shows the signal response data at 450 nm. As expected, TS1 (which is ssDNA) provided the best signal across all methods, and the detection limit of the target DNA was ~6000 molecules (Table 3). Detection at this level could also be observed visually (FIG. 2) relative to the scrambled control SS1. Through the course of these studies, however, it became clear that detection between 6000 and $10^8$ molecules of TS1 was only qualitative and could not be used to determine the precise quantity of DNA. Quantitative detection in this system begins at $10^8$ molecules of TS1, and continues well into nM concentrations. Across the entire range of concentrations a scrambled control DNA sequence (SS1) gave no signal, demonstrating that the PNA probes are highly specific to the target DNA. In addition, signal resulting from PNA hybridization to target DNA was not affected if additional washes of the plate were performed, indicating that the PNA:DNA complex was tightly bound.

TABLE 3

Detection of Nucleic Acids by PNAs[a]

| | | Lower Limit of Qualitative Detection | | Lower Limit of Quantitative Detection | |
|---|---|---|---|---|---|
| Name | Nucleic Acid Type | Template (SP1-RP1) | Crosslink (SP3-RP3) | Template (SP1-RP1) | Crosslink (SP3-RP3) |
| TS1 | DNA (27 bp) | $6.02 \times 10^3$ | $4.15 \times 10^6$ | $1.13 \times 10^8$ $(1.09 \times 10^8)$[c] | $6.62 \times 10^8$ |
| TS2 (ds) | DNA (27 bp) | $6.02 \times 10^3$ | $4.15 \times 10^6$ | $2.53 \times 10^8$ $(2.19 \times 10^7)$[c] | $9.03 \times 10^8$ |
| TS3 (ds) | DNA (50 bp) | $2.14 \times 10^7$ | x | $4.49 \times 10^9$ | x |

[a]Unless otherwise noted, values were determined by curve fits to VMax (mAbs 652 nm * $min^{-1}$) vs. [DNA] data.
[b]Values for quantitative detection are the number of molecules detected at 90% CI and 96% minimal distinguishable difference concentration.
[c]Values determine from curve fit to absorbance at 450 nm vs. [DNA].

While detection of ssDNA is useful to explore the capabilities of PNA probes, a diagnostic device would have to bind the target sequence even if it is bound to its complementary sequence in a dsDNA complex. Commercial kits that are used to isolate DNA from samples for diagnostic analysis usually provide low molecular weight dsDNA fragments of highly variable sizes. Therefore, we investigated whether our assay could detect dsDNA. While PNA can invade dsDNA in some cases, we employed snap cooling to separate the complementary DNA strands and allow the PNA probes to compete for the target. Detection of the double stranded target (TS2, Tm=55° C.) by following the development of signal at 652 nm (FIG. 2C) showed a detection similar to TS1 (qualitative detection at about 6000 molecules, quantitative detection starting around 108 molecules). Interestingly, the quantitative detection limit was lowered to 107 molecules when following the signal at 450 nm. The qualitative detection of a significantly longer dsDNA sequence (in this case a 50-bp fragment with the target sequence embedded within a central position in the DNA fragment (TS3, Tm=65° C.)) rises to 107 molecules, and the quantitative detection limit increases to 109 molecules of dsDNA. While not wanting to be bound by theory, this change is likely due to the increased stability of the DNA duplex that contains the target sequence.

One experimental example of a method for detecting a nucleic acid of interest comprises obtaining a solution in which the presence of a nucleic acid of interest will be determined; obtaining a capture probe PNA (PNAα) substrate comprising (i) at least one nucleobase sequence that is complementary to at least one first nucleic acid sequence on the nucleic acid of interest, (ii) at least two trans-cyclopentanes (or 3 or more), and (iii) wherein the PNAα is bound to a substrate; obtaining a detection probe PNA (PNAβ) comprising (i) at least one nucleobase sequence that is complementary to a second nucleic acid sequence on the nucleic acid of interest that is different from the first nucleic acid sequence, and (ii) at least six biotin groups (or 12 or more, or 18 or more); contacting the solution in which the presence of a nucleic acid of interest will be determined with (i) the capture probe PNA (PNAα) substrate and (ii) the detection probe PNA (PNAβ); and detecting the presence of the biotin-labeled detection probe PNA (PNAβ) bound to the capture probe PNA (PNAα) substrate.

In some experiments, the substrate is visually observed to detect the appearance of a detectable signal from the reporter molecule, and also the substrate may be washed prior to determining the presence of the reporter molecule. Actual detection of the presence of a pathogen nucleic acid may be observed visually with or without the aid of a device such as a spectrometer.

In other experiments the choice of label on the reporter group may vary, as long as it provides sufficient signal to provide qualitative and/or quantitative detection. For example, the detection probe PNA (PNAβ) biotin groups may be conjugated to any avidin-based signaling composition, such as horseradish peroxidase-avidin conjugate, poly-horseradish peroxidase-avidin, labeled nanoparticles (such as gold or silver nanoparticles), quantum dots, fluorescent dyes, radioligands, and the like.

The methods and compositions described in this paper may be used to detect any nucleic acid of interest including nucleic acids present in any diseased tissue or organism, pathogenic organism, or non-pathogenic organism, non-limiting examples include anthrax, avian flu, influenza variants, severe acute respiratory syndrome (SARS), tuberculosis (TB), human papilloma virus (HPV), human immunodeficiency virus (HIV) (including HIV gag), *Legionella*, Norwalk virus, *salmonella, E. coli*, and any food-borne or water-borne pathogen.

The nucleic acid of interest may be detected in any volume of sample when 5 to 1000 copies of the nucleic acid of interest are present in the solution being tested. Furthermore, in one example, when the nucleic acid of interest is detected at about 40 to 1000 copies in the solution being tested, then the number of copies may be quantifiable as being proportional to the amount of signal detected from the reporter molecule.

The methods and compositions described in this application are useful for clinical evaluation of the presence of a quantifiable amount of a nucleic acid or pathogen of interest. For example, the methods and compositions described may provide a clinician quantification of the HIV load in an HIV patient, such as, when the nucleic acid of interest is detected in a patient at a quantifiable level of less than 50 copies per ml of biological sample, and the HIV status of the patient is then categorized as dormant or in remission. Also, the nucleic acid of interest may be detected in a patient at a quantifiable level of greater than 300 copies per ml of biological sample, and the HIV status of the patient is then categorized as active or in relapse.

Figure 3:
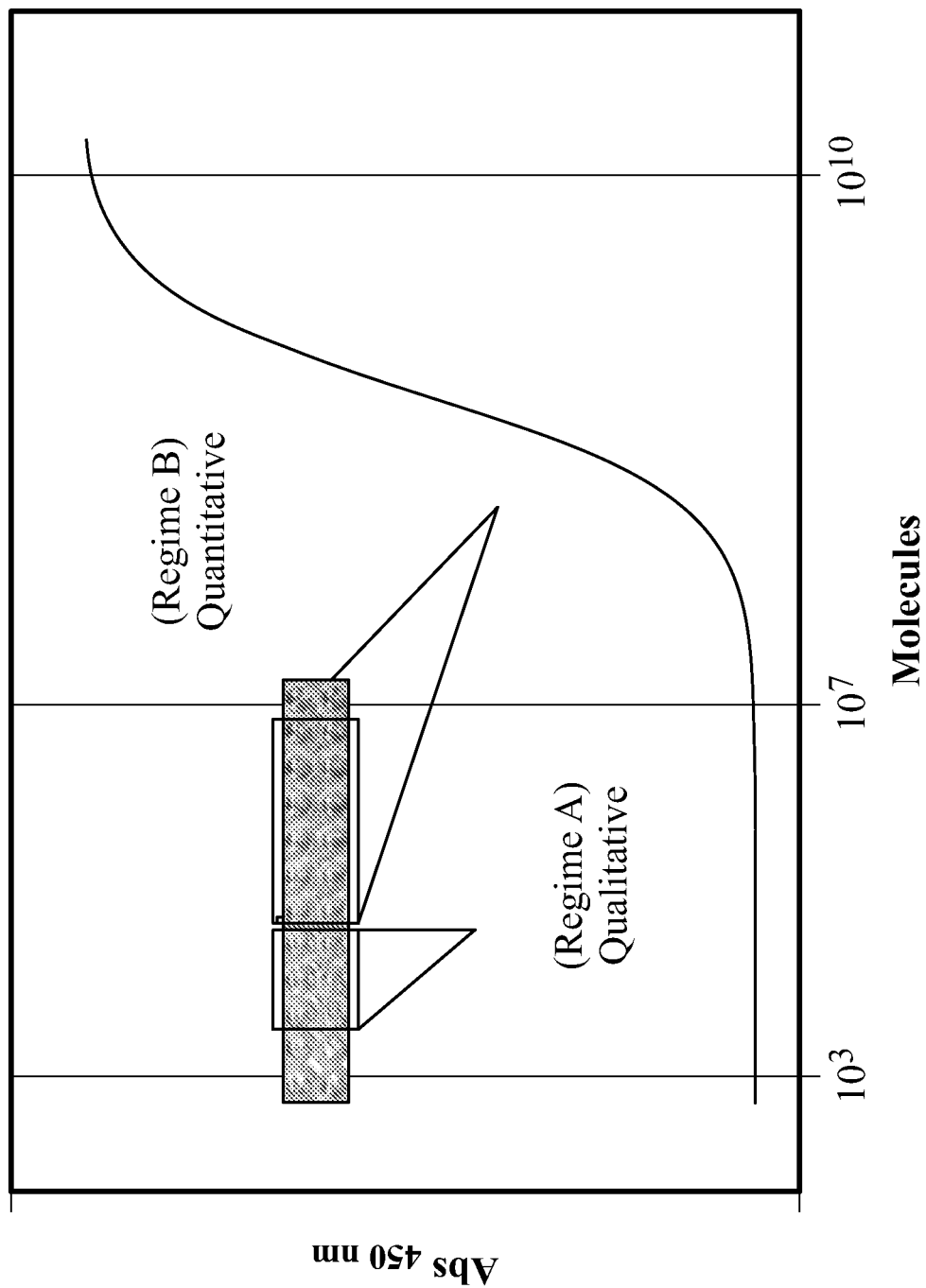
FIG. 3 presents quantitative vs. qualitative detection regimes for PNA probes. In regime A, only the presence of DNA, but not the amount can be detected. In regime B, the presence and amount of DNA can be detected.
Figure 4:
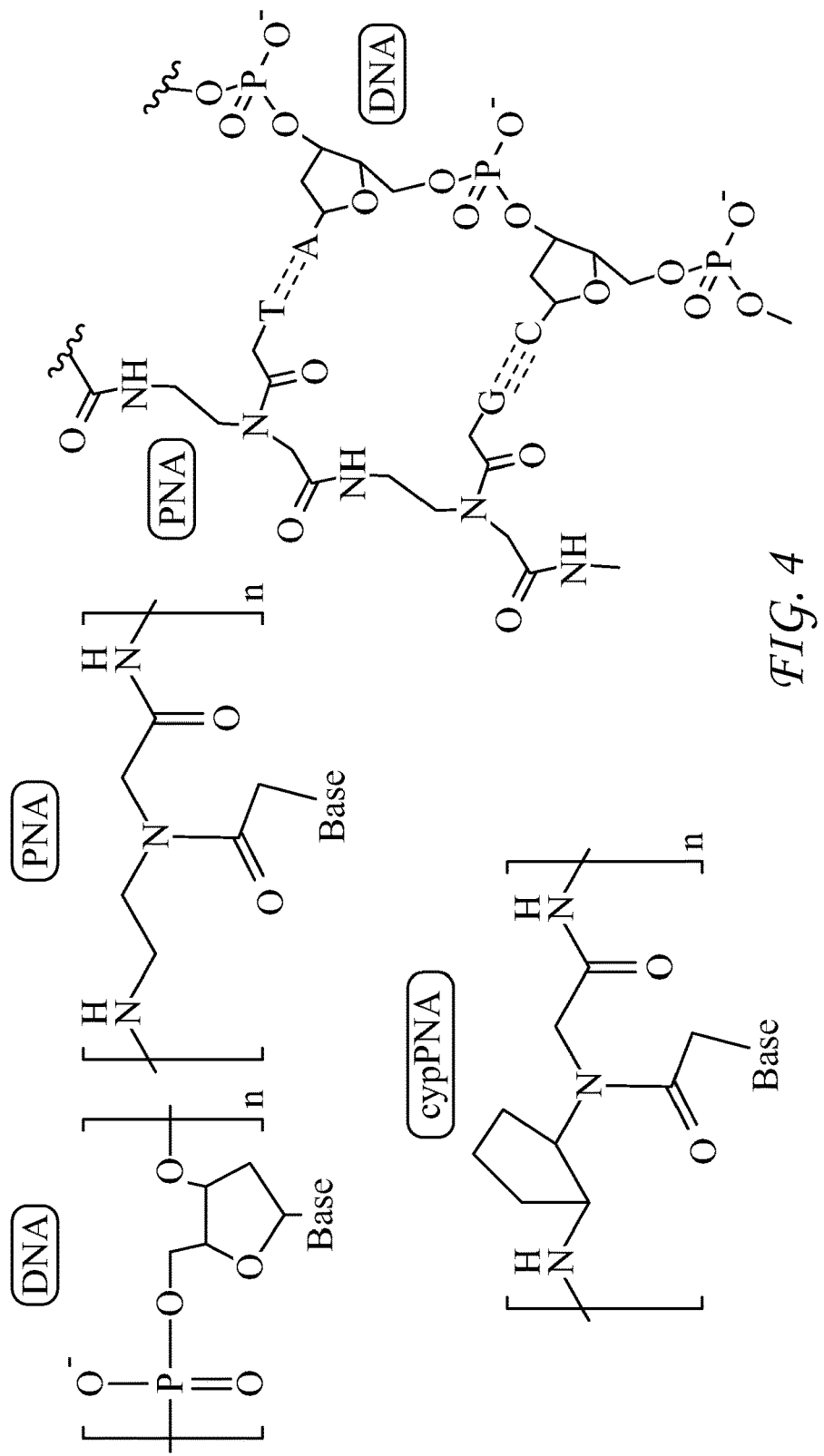
FIG. 4 shows the chemical structure of DNA, PNA, cypPNA, and PNA Watson-Crick base paring with DNA.
Figure 5:
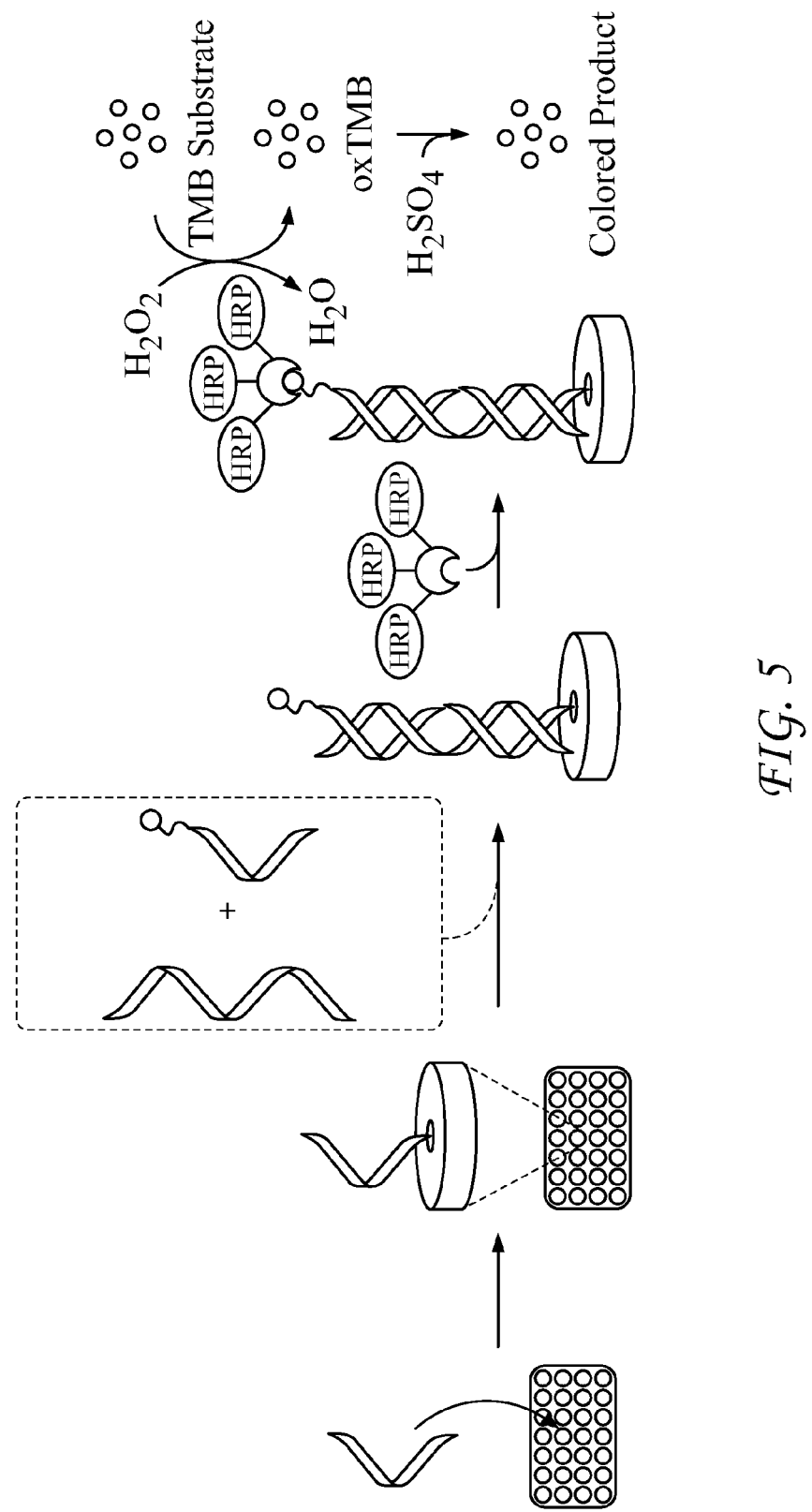
FIG. 5 presents a schematic of sandwich-hybridization assay with PNA probes.
Figures 6, 6A:
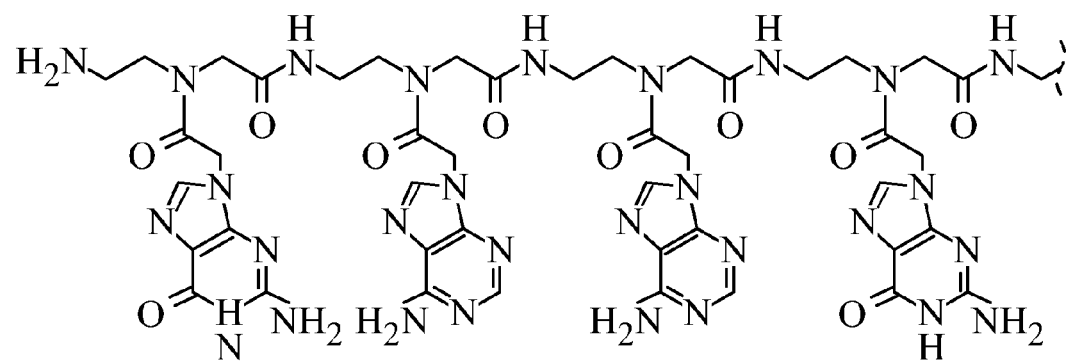
FIG. 6 shows Reporter Probe 6 (RP6).
Figure 6B:
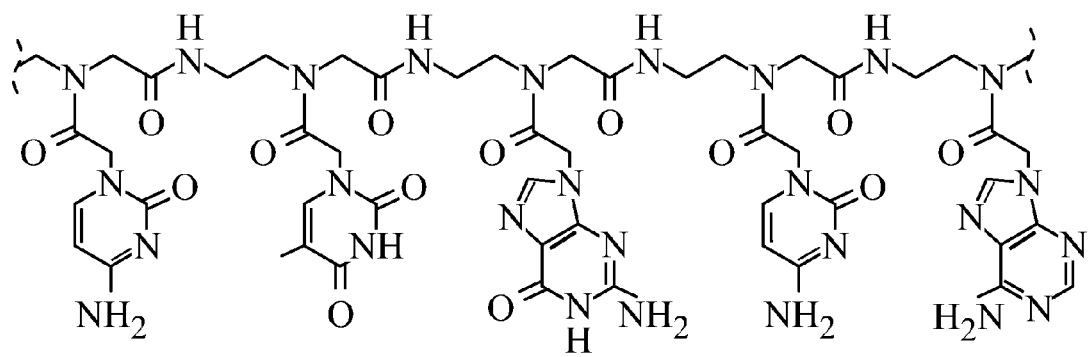
Figure 6C:
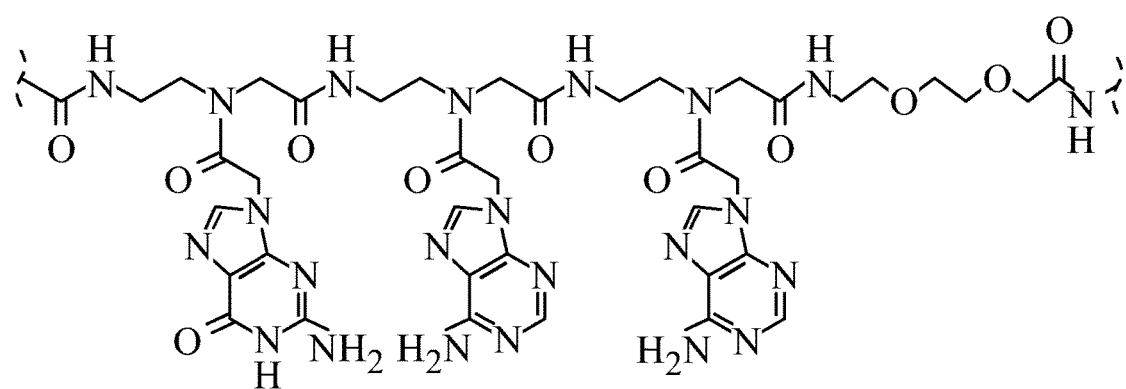
Figure 6D:
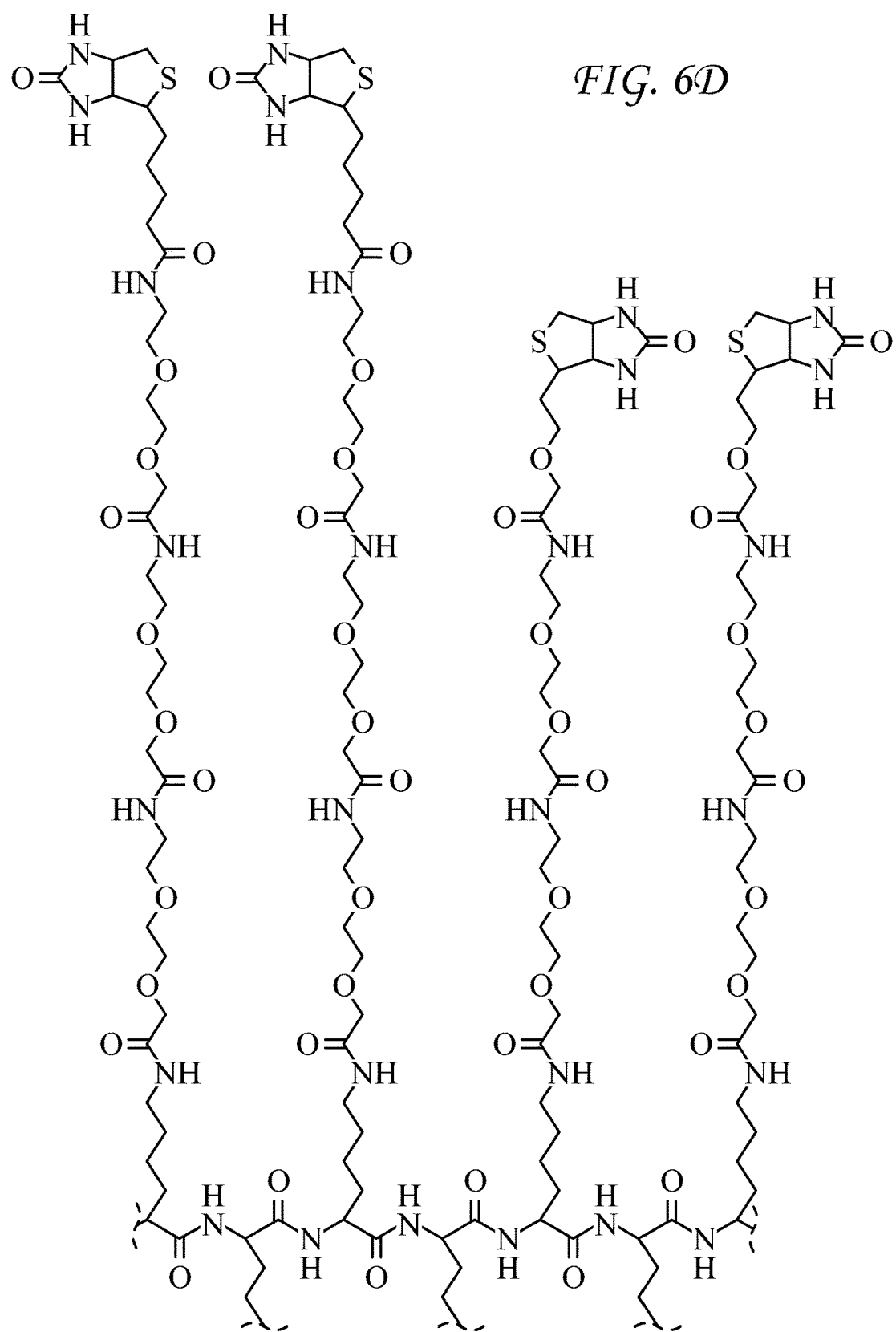
Figure 6E:
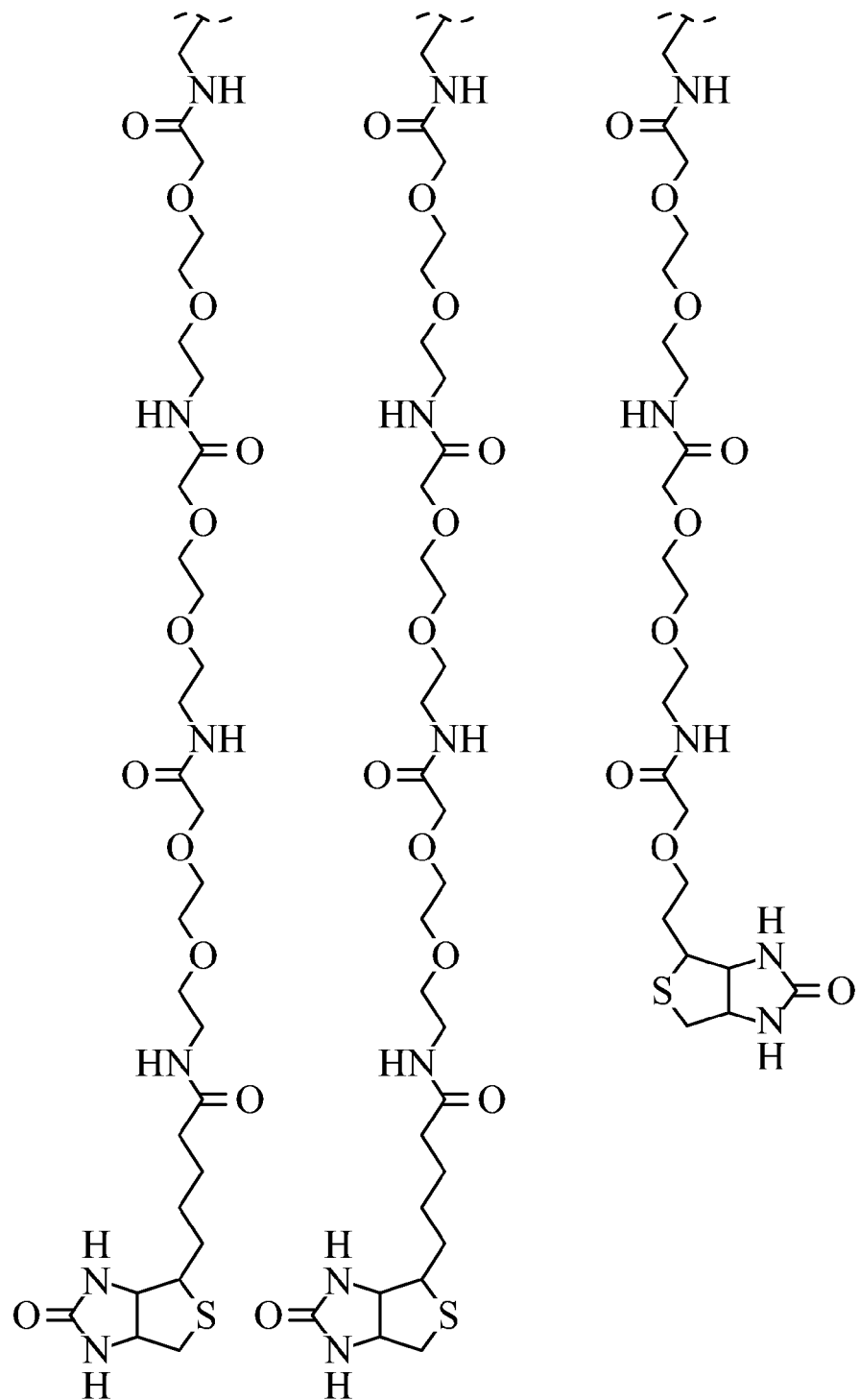
Figure 6F:
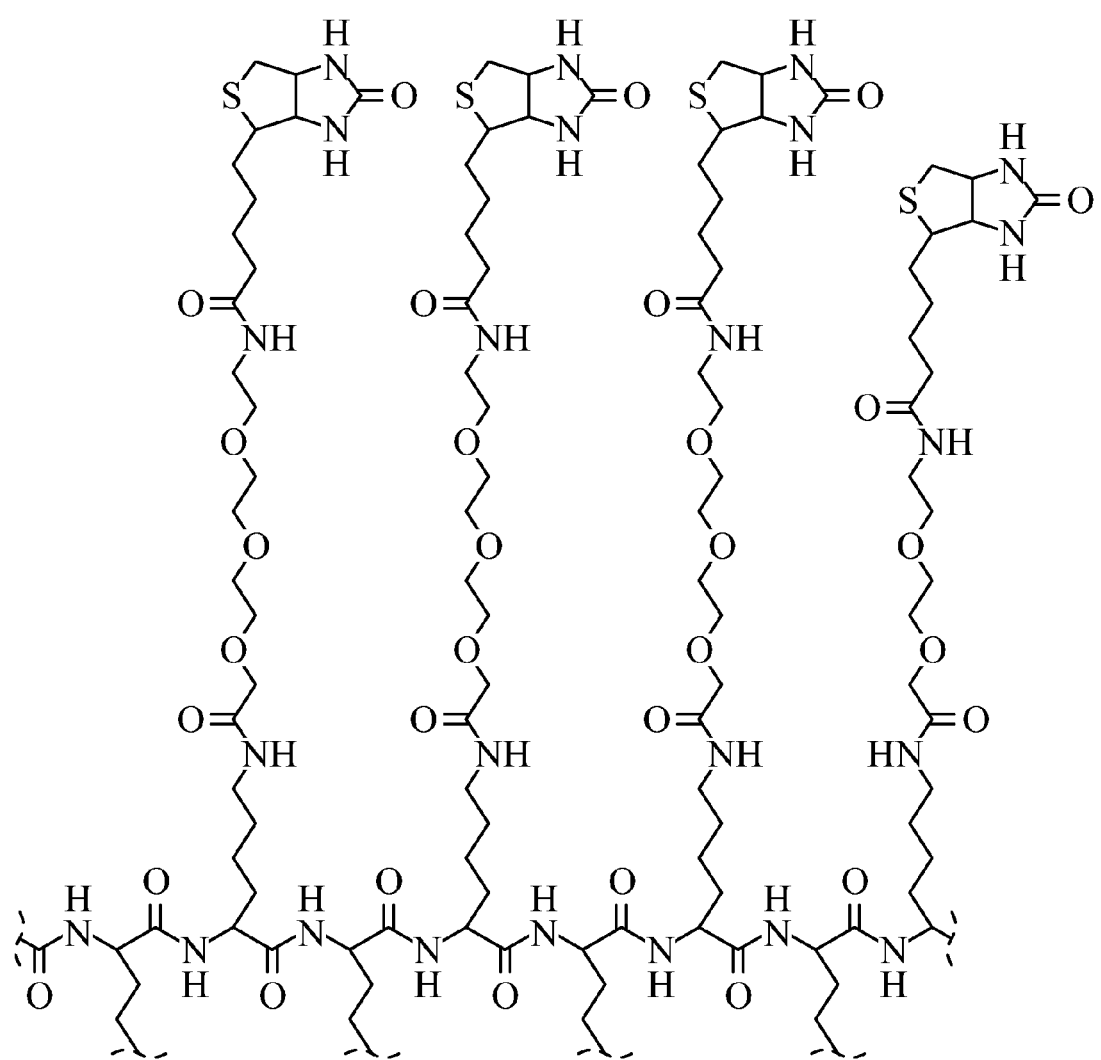
Figure 6G:
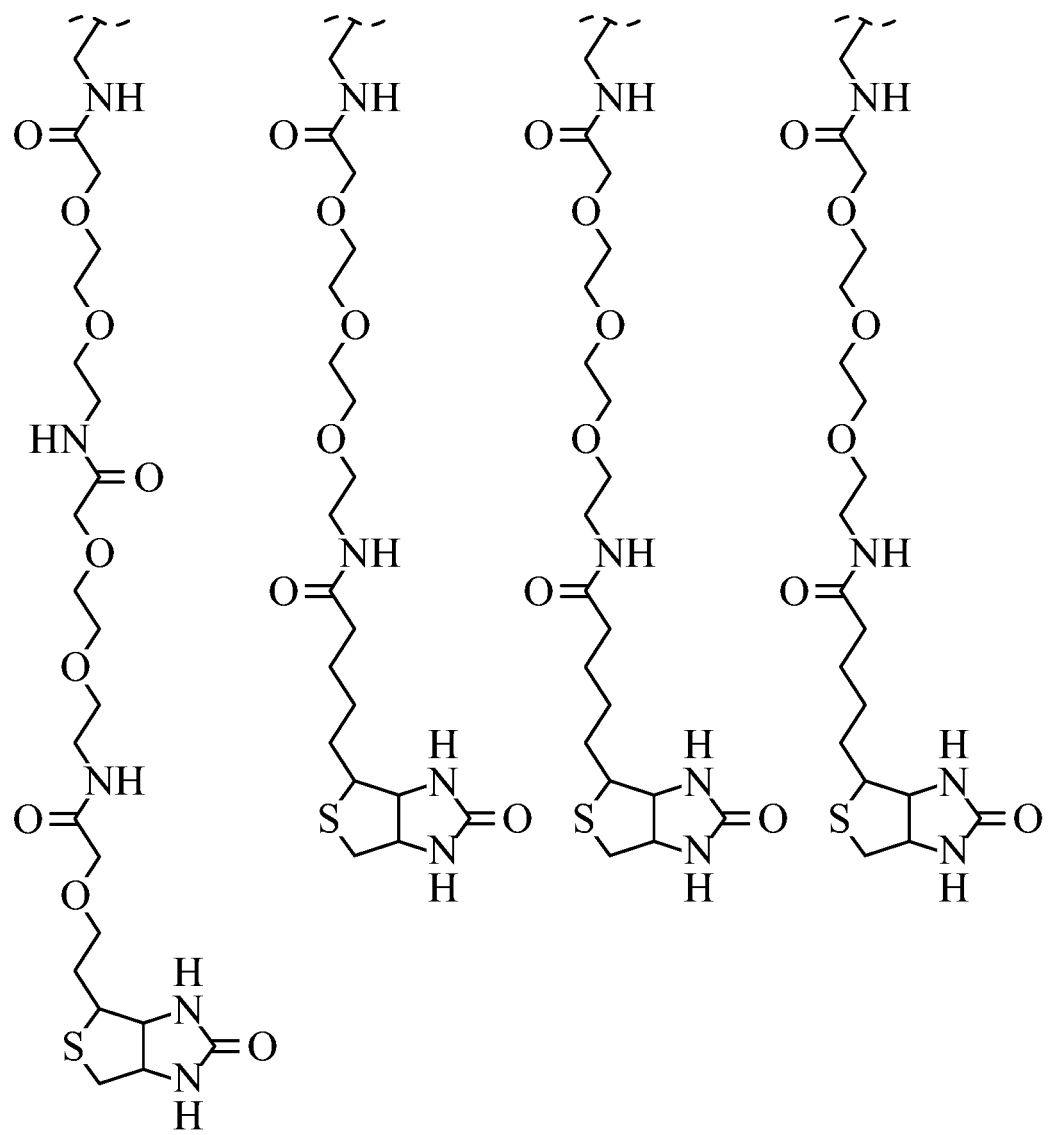
Figure 6H:
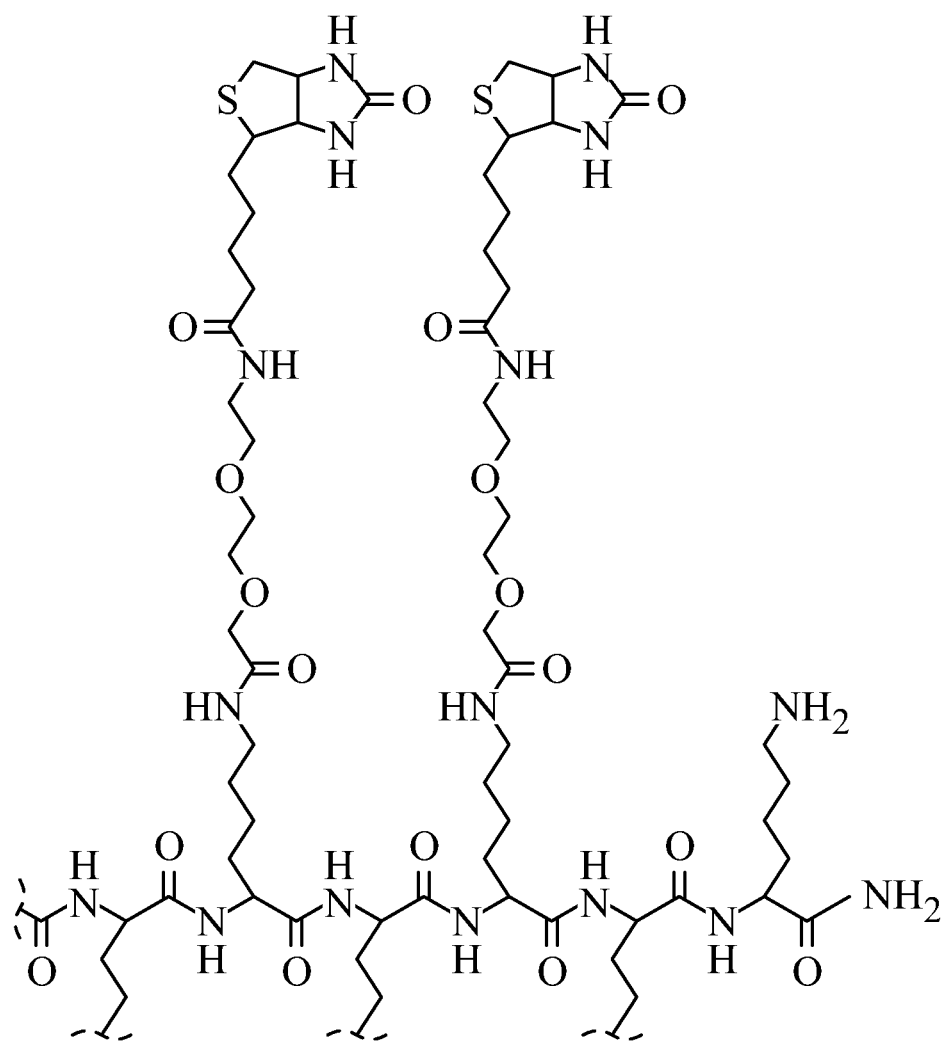
Figure 6I:
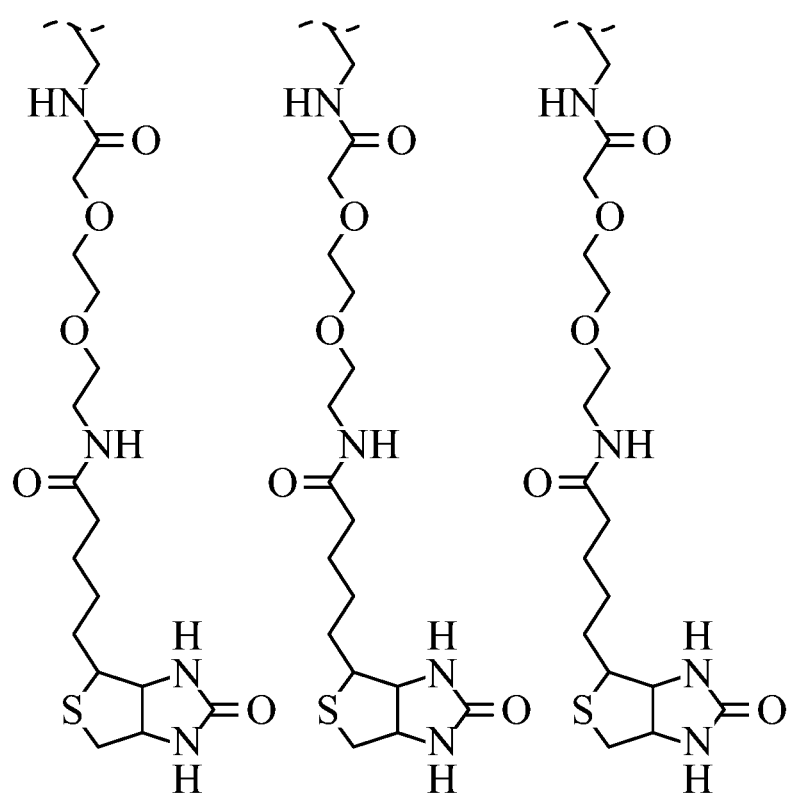
Figures 7, 7A:
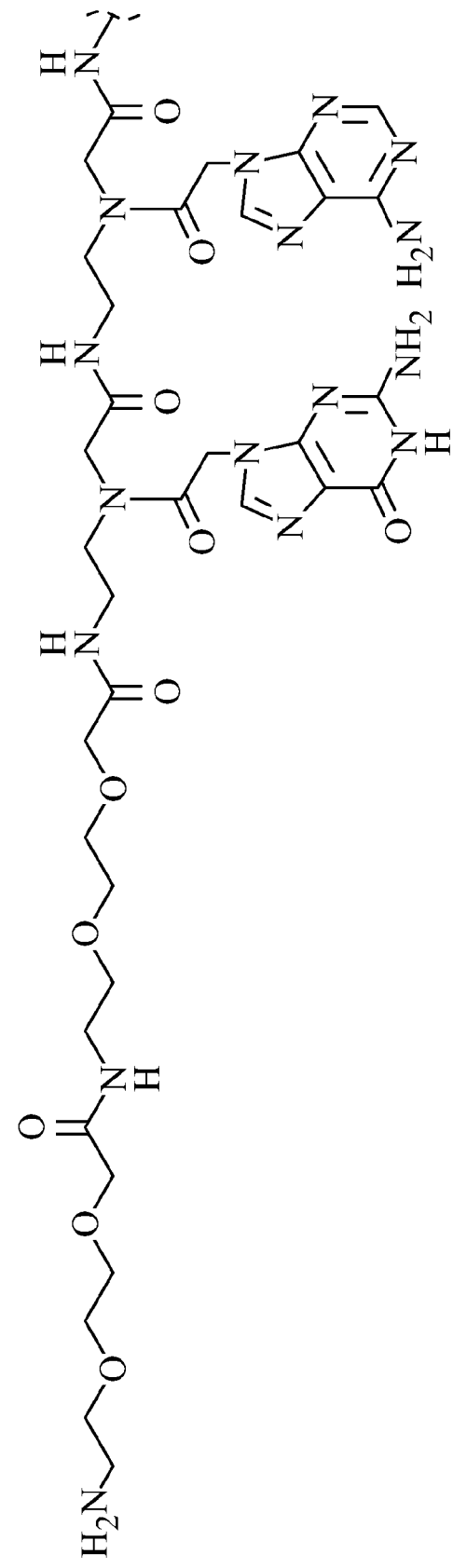
FIG. 7 shows Surface Probe 6 (SP6).
Figure 7B:
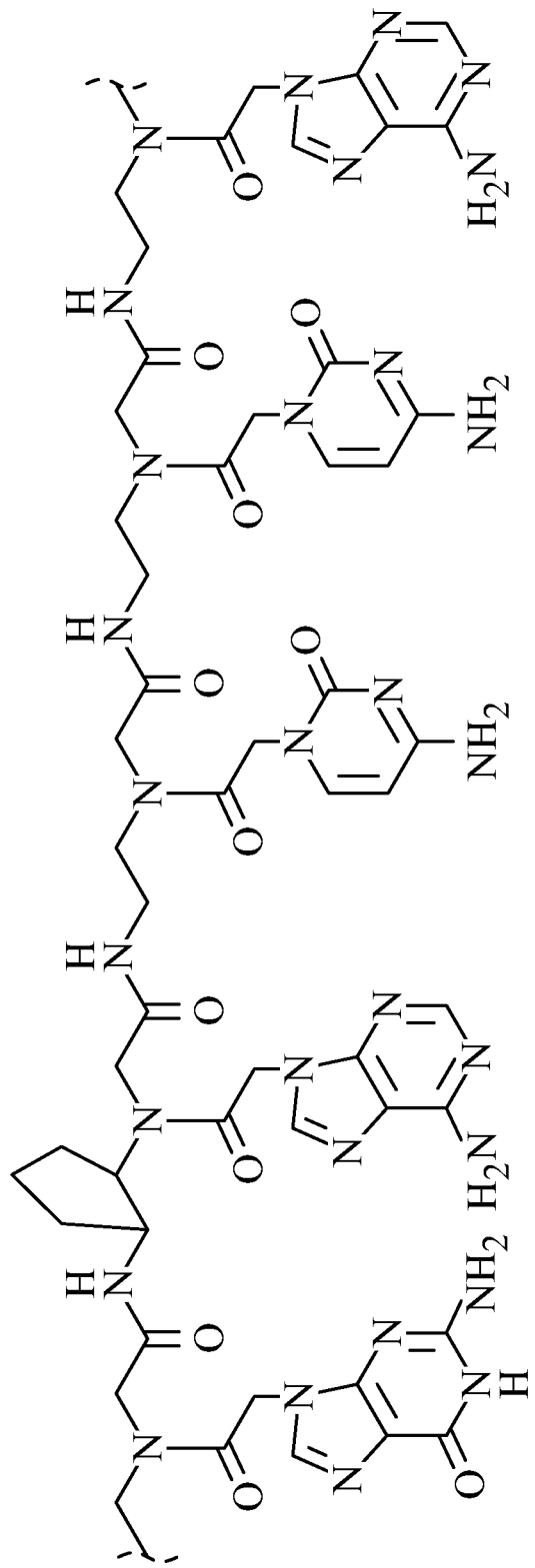
Figure 7C:
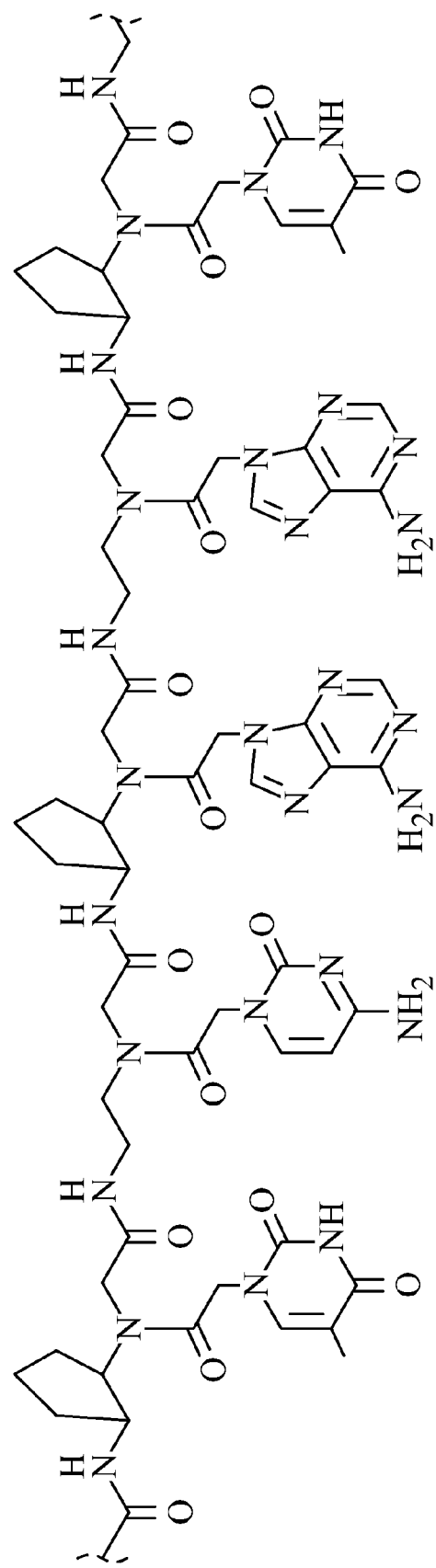
Figure 7D:
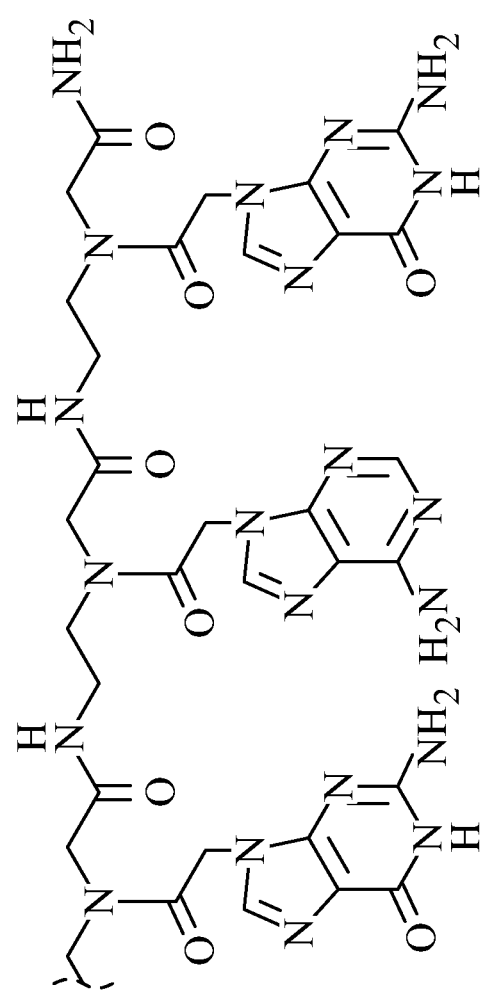
Figure 8:
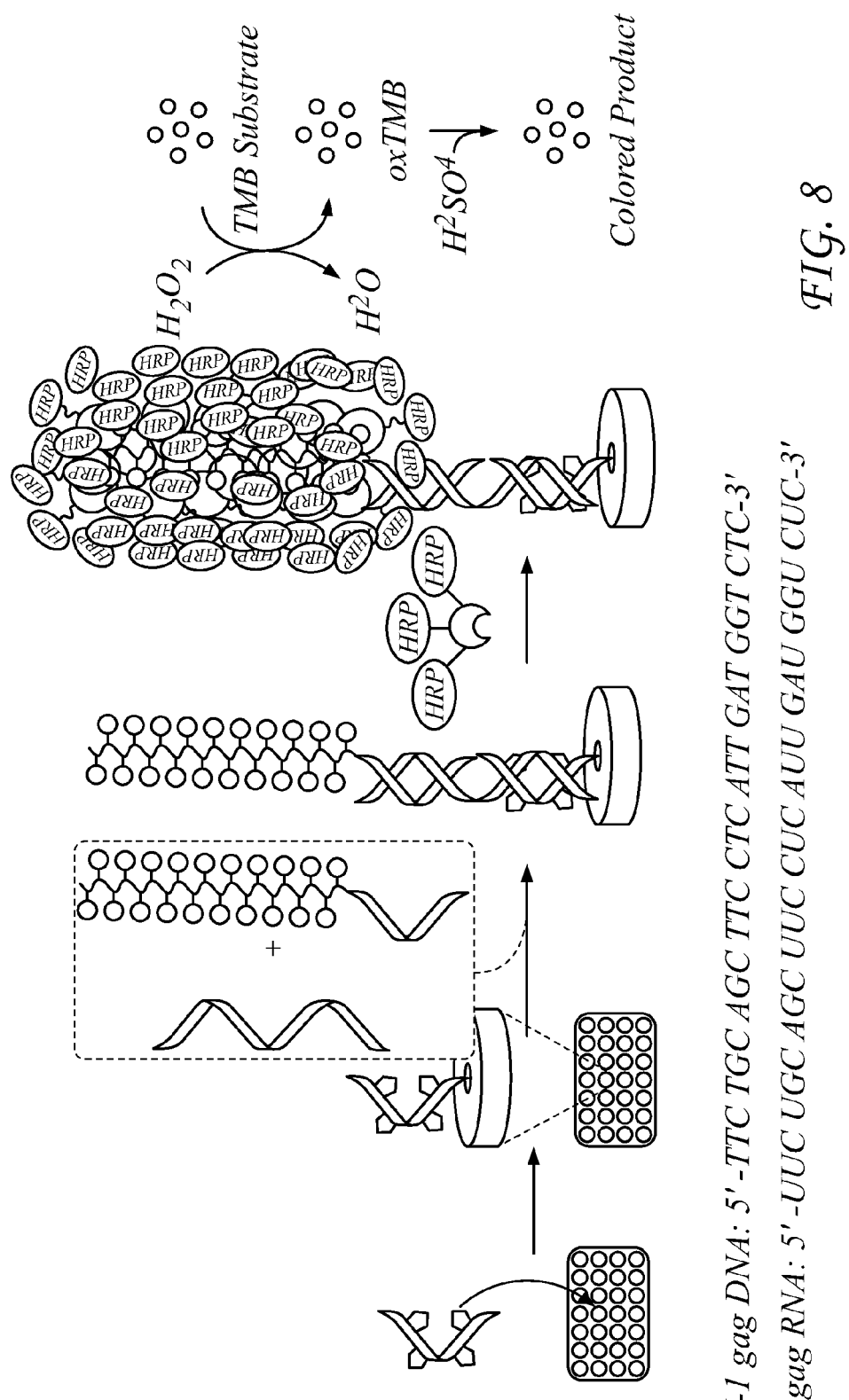
FIG. 8 illustrates an embodiment of the detection principle.

The stability of PNA probes allows for rugged devices for genetic detection. We have demonstrated that PNAs can be used as probes to signal the presence of DNA in both a qualitative and quantitative manner. Our method allowed us to identify double stranded DNA, which is important because DNA extracted from samples would contain fragments of double stranded DNA. The chemical crosslink between PNA probes provides a lasting link to the source of the initial sample so that additional assays no longer depend on the integrity of DNA collected at the sample site. We have demonstrated the ability to quantitatively detect tens of millions (107) of dsDNA copies (FIG. 3, regime B). Below this threshold, signal is qualitative and could be used to confirm the presence of DNA, but not the amount (FIG. 3, regime A). While the ELISA-based components of this detection system are not suitable for incorporation into a rugged diagnostic kit and the detection levels are not sufficient for use in the field, the well-established protocols associated with ELISA detection allow one to fully characterize the nucleic acid detection properties of different PNA probes prior to incorporation into a new technological platform.

We believe that current and future detection technologies for anthrax, as well as other pathogens, should consider using PNA as probes for nucleic acids. In particular, researchers developing new diagnostic platforms involving nanotechnology and microfluidics should consider incorporation of PNA probes into their design criteria to signal the presence of a pathogen. For this area, we feel it is important to have a general method to initially confirm the utility of any new PNA probe using standard procedures. The data in this application provides the basic method that can be used to validate sets of PNA probes before incorporation into a new type of technology for signal detection.

Experimental Detail

Abbreviations:

(ACN) acetonitrile; (BLB) 2% BSA, 25 mM Tris, 150 mM NaCl, 0.05% TWEEN 20 (i.e., polyoxyethylene (20) sorbitan monolaurate), 0.1 mM EDTA, pH 7.4; (BLBs) BLB with 0.1 .mu.g/mL single stranded salmon sperm DNA; (BSA) bovine serum albumin; (CAP) 25 mM Lys, 10 mM $NaH_2PO_4$, 100 mM NaCl, 0.1 mM EDTA, pH 8.0; (DCM) dichloromethane; (DIEA) N,N-diisopropylethylamine; (DMF) N,N-dimethylformamide; (DTDP) 2,2'-dithiodipyridine; (DTT) dithiothreitol; ($Et_2O$) diethyl ether; (HATU) O-(7-azabenzotriazol-1-yl)-N,N,N,N-tetramethylammoniumhexafluorophosphate; (HBTU) O-benzatriazole-N,N,N,N-tetramethyluroniumhexafluorophosphate; (IB) immobilization buffer (100 mM $Na_2CO_3$, pH 9.6); (MBHA) methyl-benzhydrylamine; (pHRP) poly-horseradish peroxidase; (EDTA) sodium salt of ethylene-diaminetetraacetic acid;

(NMP) N-methyl-2-pyrolidinone; (PBS) phosphate buffered saline solution; (PBST) PBS with 0.05% TWEEN 20; (mPEG) 8-amino-3,6-dioxaoctanoic acid; (NHS) N-hydroxysuccinimide; (PNA) peptide nucleic acid; (RT) room temperature; (SA) streptavidin; (SPPS) solid-phased peptide synthesis; (TEMED) Tetra-methylethylenediamine; (TFA) trifluoroacetic acid; (TFMSA) trifluoromethanesulfonic acid; (TIPS) triisopropylsilane; (TMB) 3,3'5,5'-tetramethylbenzdine; (Tris) tris(hydroxy-methyl)aminomethane; (TWEEN 20) polysorbate 20.

Reagent Sources:

All Boc- and Fmoc-peptide nucleic acid monomers were purchased from Applied Biosystems (Carlsbad, Calif.) or PolyOrg, Inc. (Leominster, Mass.); cyclopentane T PNA monomer was made following previously published procedures, ACN, BSA, DCM, DIEA, DMF, DTDP, EDTA, $Et_2O$, 1M DTT (in water), Kaiser test reagents, m-cresol, MeOH, NaCl, $Na_2CO_3$, NMP, $NaH_2PO_4$ piperidine, plate seal film, ssDNA, TFA, TFMSA, TIPS, thioanisole, TWEEN 20 were purchased from Sigma-Aldrich (St. Louis, Mo.). 1-Step™ Ultra-TMB, 96-well Nunc Immobilizer Amino plates, NHS ester of $PEG_4$ maleimide, pHRP linked SA, and TMB Stop Solution were obtained from Thermo Scientific (Fairlawn, N.J.); PBS buffer was purchased from Quality Biological (Gaithersburg, Md.); High purity water (18 MΩ) was generated from a Millipore (Billerica, Mass.) MilliQ water system. HATU was purchased from Applied Biosystems; Boc- and Fmoc-mPEG-OH (t-butyloxycarbonyl- or 9-fluorenylmethoxycarbonyl-8-amino-3,6-dioxaoctanoic acid and $Boc-mPEG_3-OH$ (t-butyloxycarbonyl-11-amino-3,6,9-trioxaundecanoic acid) were purchased from Peptides International (Louisville, Ky.); HBTU, Boc-Lys(Fmoc)-OH, Fmoc-Lys(Boc)-OH, H-Lys-OH.HCl, MBHA resin were purchased from Advanced Chemtech (Louisville, Ky.). $H_2SO_4$ was purchased from EMD Chemicals (Gibbstown, N.J.). Synthetic control and target DNA's were purchased from Integrated DNA Technologies (Coralville, Iowa).

General Method for PNA Synthesis:

PNA's were prepared on 5 or 25 μmol scale using either Boc- or Fmoc-SPPS on an Applied Biosystems 433a automated peptide synthesizer using HBTU activation. All PNA's were synthesized on Lys downloaded MBHA resin or modified resin (see below).

Resin Downloading Protocol:

MBHA resin was downloaded from 0.3 mmol/g to 0.1 mmol/g using Boc-Lys(2-Cl-Z)—OH. 1.0 g of resin was swelled with DCM for 1 h in a peptide synthesis vessel. The following solutions were prepared: (A) 0.4 M Boc-Lys(2-Cl-Z)—OH in NMP, (B) 0.2 M HATU in DMF, and (C) 0.5 M DIEA in NMP. 450 μL (A), 460 μL (C) and 1.59 mL NMP were combined and mixed (Solution 1) and 550 μL (B) were diluted with 1.95 mL NMP (Solution 2). Solutions 1 and 2 were combined and pre-mixed for ~30 s before adding to the drained, swelled resin. The resin/coupling mixture was agitated for 1 h before draining and washing with DMF (4×), DCM (4×), 5% DIEA in DCM (1×-30 s) and finally DCM (4×). Any remaining active sites were capped using capping cocktail (1:25:25 $Ac_2O$:NMP:pyridine) for 20 min. The reaction was drained and rinsed with DMF (3×) and DCM (3×). The progress of the capping was followed by qualitative Kaiser test. If the test was positive, the resin was resubmitted to capping. After a negative test for primary amines, the resin was washed with DCM (3×) and dried under vacuum for 30-60 min and then stored in a desiccator.

Cleavage and Recovery of Crude PNA from Resin:

The resin, in a peptide synthesis vessel, was first washed with TFA (2× for 4 min). To the drained resin, cleavage cocktail (1.5 mL, 60:20:10:10 TFA/TFMSA/thioanisole/m-cresol), cooled over ice, was added and reacted for 1 h. The cleavage mixture was collected in a glass vial using $N_2$ pressure to drain the vessel. The resin was resubmitted to fresh cleavage cocktail and cleaved for 1 h, and was drained into the first cleavage fraction. The volatiles were removed by flowing dry $N_2$ over the solution to produce a yellow-brown oil.

Approximately 10 mL of $Et_2O$ was added to the cleavage oil to create a suspended white precipitate. The suspension was partitioned into five 2 mL microcentrifuge tubes and chilled over dry ice for 10 min. The tubes were centrifuged at 12,000 rpm for 40 s to produce a white pellet. $Et_2O$ was carefully decanted, leaving the white crude PNA solid. Further washing was performed by adding ~1.6 mL of $Et_2O$ to each tube, mixing to re-suspend the precipitate, and then chilling on dry ice for 5 min. Following centrifugation and decanting, the washes were repeated twice without dry ice. After the final wash, the white precipitate was dried by carefully passing a stream of dry $N_2$ over the crude PNA.

Purification of Crude PNA and Characterization:

Purification was performed on an Agilent (Santa Clara, Calif.) 1100 Series RP-HPLC with automatic (SP1, SP2, RP1 & RP2) or manual fraction collection (SP3 & RP3) using UV detection at 260 nm. Waters (Milford, Mass.) XBridge C18 (10×250 mm, 5 μm) columns were used in conjunction with Solvents A and B. Solvent A was 0.05% TFA in water and Solvent B consisted of 90% ACN in water. PNA's were purified using the following elution gradients: SP1 and RP1—(4.0 mL/min) 10% B over 5 min, 25% over 25 min and elution at 17 and 27 min, respectively; SP2—(4.5 mL/min) 0% B for 2 min, 8% over 3 min, 14% over 22 min with elution at 21 min; SP3—(4.0 mL/min) 0% B for 2 min, 15.5% over 3 min, 10.5% over 22 min with elution at 18 min; RP2—(4.0 mL/min) 0% B for 2 min, 12% for 3 min, 10% for 22 min and elution at 18 min. RP3—(5.0 mL/min) 0% B for 2 min, 28% for 3 min, 16% for 21 min and elution at 11 min. PNA HPLC isolates were characterized using ESI-MS on a Waters/Micromass LCT Premier™ time-of-flight mass spectrometer. The instrument was operated in W-mode at a nominal resolution of 10,000. The electrospray capillary voltage was 2 kV and the sample cone voltage was 60 V. The desolvation temperature was 275° C. and the desolvation gas was N2 with a flow of 300 L/h. Accurate masses were obtained using the internal reference standard method. The sample was introduced into the mass spectrometer via the direct loop injection method. Deconvolution of multiply charged ions was performed with MaxEnt I. All PNA oligomers gave molecular ions consistent with the calculated theoretical product values.

TABLE 4

PNA Molecular Weight Characterization

| Probe | Sequence | Theoretical MW | Observed MW |
|---|---|---|---|
| SP1 | H$_2$N-(mPEG)$_5$-ATCCTTAT$_{cyp}$CAATATT-CONH$_2$ (SEQ. ID. NO. 1) | 4776.7 | 4776.0 |
| SP2 | Ac-(mPEG)$_2$-ATCCTTATCAATATT-Lys(mPEG-Cys-NH$_2$)-CONH$_2$ (SEQ. ID. NO. 2) | 4719.7 | 4719.5 |
| RP1 | Ac-TAACAATAATCC-mPEG-Lys[(mPEG$_3$)$_2$-BT]-Lys[(mPEG$_3$)$_2$-BT]-Lys(mPEG$_3$-BT)-Lys(mPEG$_3$-BT)-Lys(mPEG-BT)-Lys(mPEG-BT)-Lys(mPEG-BT)-Lys(NH$_2$)-CONH$_2$ (SEQ. ID. NO. 3) | 7088.9 | 7089.0 |

Table Notes: T cyp is S,S-transcyclopentane modified thymine

TABLE 5

Nucleic Acid Sequences

| Name | Nucleic Acid Type | Sequence | # of bases |
|---|---|---|---|
| TS1 | DNA | 5'-GGA-TTA-TTG-TTA-AAT-ATT-GAT-AAG-GAT-3' (SEQ. ID. NO. 4) | 27 |
| TS2 | DNA (ds) | 5'-GGA-TTA-TTG-TTA-AAT-ATT-GAT-AAG-GAT (SEQ. ID. NO. 4)-3'<br>3'-CCT-AAT-AAC-AAT-TTA-TAA-CTA-TTC-CTA-5' | 27 |
| TS3 | DNA (ds) | 5'-GCTGAAATATAGGATTATTGTTAAATATTGATAAGGATG TAATGATAATA-3' (SEQ. ID. NO. 5)<br>3'-CGACT TTATATCCTAATAACAAT TTATAACTAT TCCT ACAT TACTAT TA-5' | 50 |
| SS1 | DNA | 5'-TGC-AGT-CTG-TTA-CAA-TGA-CCT-ACT-3' (SEQ. ID. NO. 6) | 24 |
| SS4 | DNA (ds) | 5'-GCTGAAATATAAAGATAAATAGGTGTCAATTGTAGAACG TAATGATAATA-3' (SEQ. ID. NO. 7)<br>3'-CGACT TTATATT TCTATTTATCCACAGT TAACATCT TGCATTACTATTAT-5' | 50 |

Thermal Melting Analysis:

UV concentration determination was determined by adding 1 μL of nucleic acid solution to 175 μL milliQ water, unless the concentration was too intense and consequently the 1 μL was diluted with 351 μL of water. Water was blanked against the background at 80° C. on an Agilent 8453 UV/Vis spectrometer equipped with an Agilent 89090A peltier temperature controller and a computer interface. Then the unknown solution was added to the quartz cell (Helma) and vigorously shaken, replaced in the spectrophotometer and the absorbance was read at 260 nm. The mixing and reading was repeated 3 more times. Values were converted to concentration, based on average absorbance. After initial measurement by UV, the concentration was determined based on appropriate ε260 (calculated on nearest neighbor approximation for PNA or provided by IDT or Thermo Scientific for oligonucleotides) and then used from that point forward for additional experiments.

Thermal melting experiments were performed by preparing 0.5-5.0 μM oligonucleotide solution in 1×PBS. Experiments traversed from 90° C. to 20° C. and back to 90° C. at 1° C. intervals while monitoring at 260 nm. An equilibration of 60 s at each temperature measurement step before readings was employed. Cooling and heating profiles were generated for each run with duplicates for each. The T$_m$ (melting temperature) for duplexes was determined using the maximum derivative of the cooling and heating curves, then taken as an average of both runs.

TABLE 6

Oligonucleotide Thermal Melting Temperatures

| Oligonucleotide Set | # of bp's | T$_m$ | Concentration[1] |
|---|---|---|---|
| TS1 (ss) | 27 | 72.7° C. | 1.0 μM |
| TS2 (ds) | 27 | 54.6° C. | 1.0 μM |
| TS3 (ds) | 50 | 64.6° C. | 0.5 μM |
| SP1/TS1 | 15 | 52.9° C. | 1.0 μM |
| SP2/TS1 | 15 | 43.8° C. | 1.0 μM |
| RP1/TS1 | 12 | 50.3° C. | 1.0 μM |
| SS1/SP1 | 15 | — | 1.0 μM |
| SS1/RP1 | 15 | — | 1.0 μM |
| SS1/SP3 | 12 | — | 1.0 μM |
| SS1/RP3 | 12 | — | 1.0 μM |

[1]Concentration of individual sequence(s).

Nucleic Acid Detection Protocol
Plate Preparation:

Surface probe (SP) was dissolved in IB [1.0 μM] with 100 μL added to each well of the plate. Blanks were left untouched throughout the process to blank against the plate. The plate was sealed with film and stirred on a plate shaker (600-700 rpm) for 2 h at RT. Then 50 μL of CAP was added to modified wells to give a final volume of 150 μL. This was again stirred at RT on a plate shaker for 30 min. Modified wells were then aspirated and washed four times with 300 μL 1×PBST and four times with 1×PBS. A final addition of 250 μL of 1×PBS was used to store the wells until used in experiments.

When the assay was ready to be performed, the 1×PBS was aspirated and 200 μL BLBs was added to the wells. The plate was sealed and incubated with shaking for 30 min at 37° C. The wells were immediately aspirated and ready for sample addition.

Sample Preparation:

All samples were prepared in glass vials. Reporter probe (RP) dissolved in 1×PBS [15 nM] was used to perform a serial dilution of the initial DNA target solution (TS). The number of samples and replicates was 10 concentrations and n=2. The initial DNA sample consisted of 600 μL PBS buffer. This initial sample was made from a DNA solution prepared from the known UV DNA solution due to the high dilution factor. (1 μL known DNA solution>50 nM DNA solution>1st sample solution) For a 3:1 dilution, 200 μL of the sample solution was removed and added to 400 μL of PBS buffer to give the dilution (e.g. 450 pM to 150 pM). Following the dilution, the samples were snap cooled by placing the vials in a 95° C. sand bath for 5 min then placing them into an ice bath for 5 min before adding to the plate. Once the samples were prepared, 100 μL of each sample was individually added to a well of the prepared plate with a 200 μL pipette, with one well acting as 1 replicate. After the samples were added to the wells, the plate was sealed and shaken for 3 h at 37° C. After incubation, if cross-linked PNA's were used, 50 μL of 3 mM DTT (in 1×PBS) was added to each well to give a final volume of 150 μL and concentration of 1 mM. The plate was shaken for 30 min and then aspirated. If no crosslinking was performed, the experimental wells were aspirated following incubation. The washing procedure consisted of 300 μL four times with 1×PBST and four times 1×PBS.

ELISA Protocol:

The wells were incubated with 200 μL of BLB. The plate was sealed and shaken at 37° C. for 30 min. Wells were then aspirated, followed by addition of 100 μL 0.1 μg/mL pHRP-SA in BLB. The plate was sealed and incubated for 20 min at RT before aspirating. The wells were aspirated and followed a washing procedure that consisted of 300 μL four times of 1×PBST and four times of 1×PBS.

ELISA Readout:

Following washes, 100 μL 1-Step™ Ultra TMB solution was added via a multitip pipetter to facilitate nearly simultaneous initial starting points for all wells. The plate was immediately placed in a Molecular Devices (Sunnyvale, Calif.) SpectraMax M5 multi-mode microplate reader and monitored at 652 nm over the course of 30 min at RT. The plate was then removed, followed by addition of 50 μL 2 M $H_2SO_4$ and mixed by hand for 10 s to quench the enzyme reaction. The plate was then returned to the plate reader and a final reading at 450 nm was performed. Plates were sealed with film following reading and placed in the refrigerator.

Analysis of Results:
Linear Regression Analysis of Absorbance (652 nm) Kinetics:

The absorbance was monitored at 2 min intervals over 30 min (16 pts) at each concentration of target nucleic acid. SoftMax Pro software was used to analyze the absorbance at 652 nm with respect to time (min). Linear regression analysis was applied to these results, ignoring any initial lag phase, using five points to return the steepest velocity ("VMax"—$mAbs_{652\ nm}$/min) over the course of the experiment. See FIGS. 2A & B for graphic examples.

Nonlinear Regression Analysis of Kinetic and Quenched Assay Results:

The calculated VMax results were used as response values and plotted with respect to target nucleic acid concentration using Prism 5.0 software. These kinetic assay results were analyzed using 4-parameter logistic (4-PL) models. The resulting fits are graphically represented in FIG. 2C and results are listed under Table 7. The protocol employing quenched TMB product used end point absorbance values at 450 nm plotted versus nucleic acid concentration and fit to a 4-PL model as for the kinetic data at 652 nm.

TABLE 7

4-PL Model Analysis of Concentration-dependent $VMax_{652\ nm}$ Results

| Name | Nucleic Acid Type Template Assay | 4-PL Model Equation | Fit |
|---|---|---|---|
| TS1 | ssDNA | y = 12.75 + ((247.3 − 12.75)/ (1 + $10^{(Log\ 0.2041-x)*0.9217}$)) | 0.979 |
| TS2 | dsDNA (27-bp) | y = 11.27 + ((172.1 − 11.27)/ (1 + $10^{(Log\ 0.1713-x)*1.487}$)) | 0.994 |
| TS3 | dsDNA (50-bp) | y = 18.39 + ((134.5 − 18.39)/ (1 + $10^{(Log\ 0.1740-x)*1.512}$)) | 0.972 |
| RS1 | ssRNA | y = 7.776 + ((126.4 − 7.776)/ (1 + $10^{(Log\ 0.1737-x)*1.927}$)) | 0.972 |

4-PL model equation: y = A + ((D − A)/(1 + $10^{(Log\ C-x)*B}$)), where A is the response at a concentration of zero (baseline); B is the slope factor; C is the inflection point ($IC_{50}$); D is the response at infinite concentration; Y is the response; X is the analyte concentration.

TABLE 8

4-PL Model Analysis of Concentration-dependent $AbS_{450\ nm}$ Results

| Name | Nucleic Acid Type Template Assay | 4-PL Model Equation | Fit |
|---|---|---|---|
| TS1 | ssDNA | y = 0.635 + ((3.65 − 0.635)/ (1 + $10^{(Log\ 0.0193-x)*1.80}$)) | 0.999 |
| TS2 | dsDNA (27-bp) | y = 1.14 + ((3.75 − 1.14)/ (1 + $10^{(Log\ 0.0107-x)*1.52}$)) | 0.994 |
| RS1 | ssRNA | y = 1.06 + ((3.68 − 1.06)/ (1 + $10^{(Log\ 0.0226-x)*2.70}$)) | 0.972 |

4-PL model equation: y = A + ((D − A)/(1 + $10^{(Log\ C-x)*B}$)), where A is the response at a concentration of zero (baseline); B is the slope factor; C is the inflection point ($IC_{50}$); D is the response at infinite concentration; Y is the response; X is the analyte concentration.
[*]Data were analyzed the day after the initial kinetic assay following washing, relabeling and a second kinetic assay, as listed under "Plate Reruns" section of SI.

Limit of Quantification (LoQ) Determination:

The limits of quantitation for the nucleic acid types investigated were determined using the 4-PL models with Prism 5.0 software by calculating the upper limit of the zero analyte concentration parameter error using a 90% confidence interval. These values provide a limit that is distinguishable from background noise with 96% certainty (minimal distinguishable differential concentration—MDDC).

Design of PNA Probes

Table 9 presents thermal melting temperature of the designed PNA probe/DNA duplexes.

TABLE 9

| PNA/DNA Duplexes | Number of Biotin | Melting Temperature |
| --- | --- | --- |
| RP1/HIV-1 gag DNA | 1 | 63.4° C. |
| RP2/HIV-1 gag DNA | 2 | 63.0° C. |
| RP3/HIV-1 gag DNA | 3 | 62.0° C. |
| RP4/HIV-1 gag DNA | 4 | 60.5° C. |
| RP5/HIV-1 gag DNA | 5 | 58.7° C. |
| RP5/HIV-1 gag DNA | 6 | 56.6° C. |

*Surface PNA probes containing different number of cyclopentane group.

| PNA/DNA Duplexes | Number of Cyclopentane | Melting Temperature |
| --- | --- | --- |
| SP1/HIV-1 gag DNA | 0 | 69.5° C. |
| SP2/HIV-1 gag DNA | 1 | 72.9° C. |
| SP3/HIV-1 gag DNA | 2 | 75.4° C. |
| SP4/HIV-1 gag DNA | 3 | 78.5° C. |
| SP5/HIV-1 gag DNA | 4 | 81.6° C. |

*Reporter PNA probes containing different number of Biotin group.

Detection Results

Figure 9A:
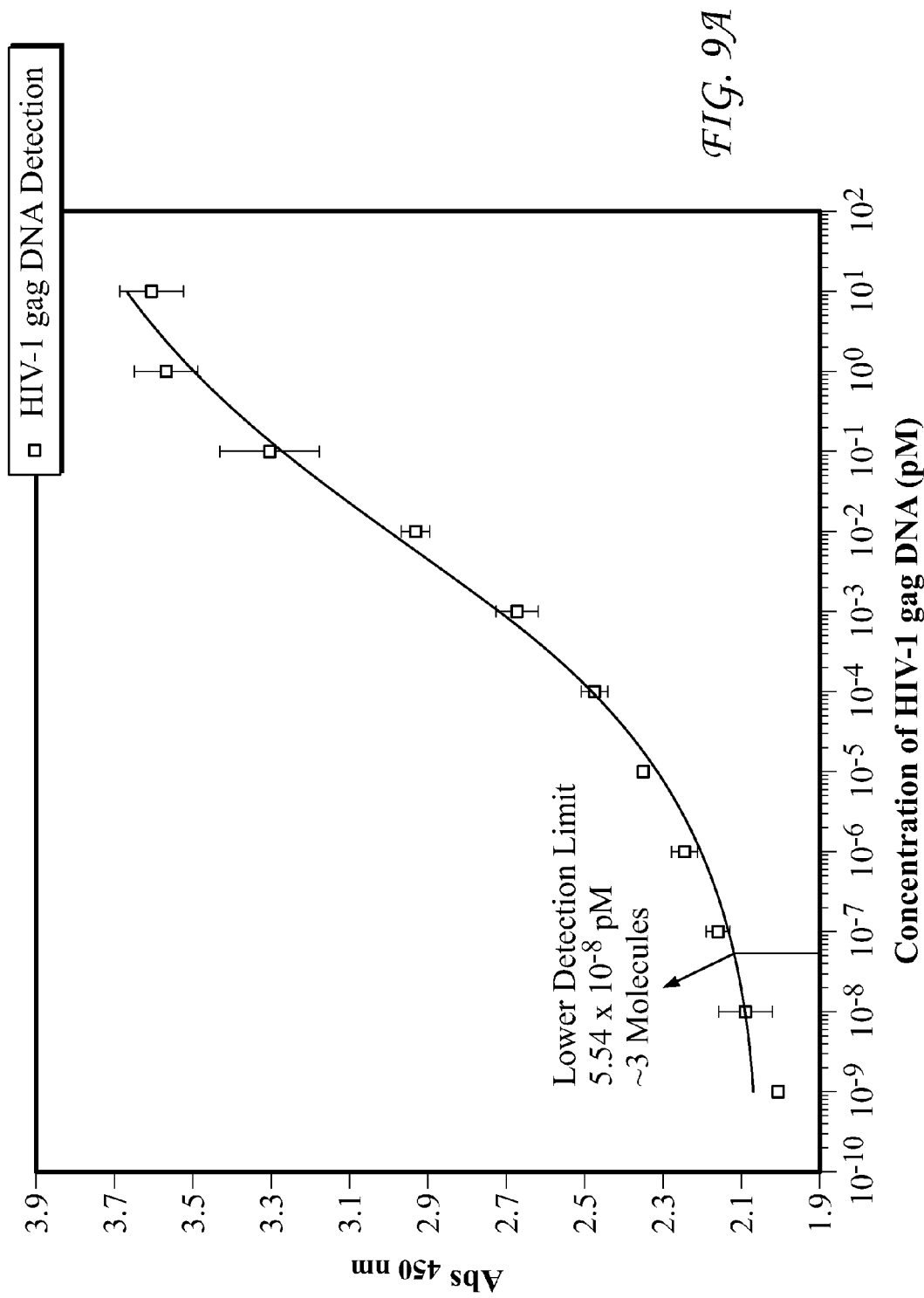
FIG. 9 presents data for HIV-1 gag DNA detection.
Figure 9B:
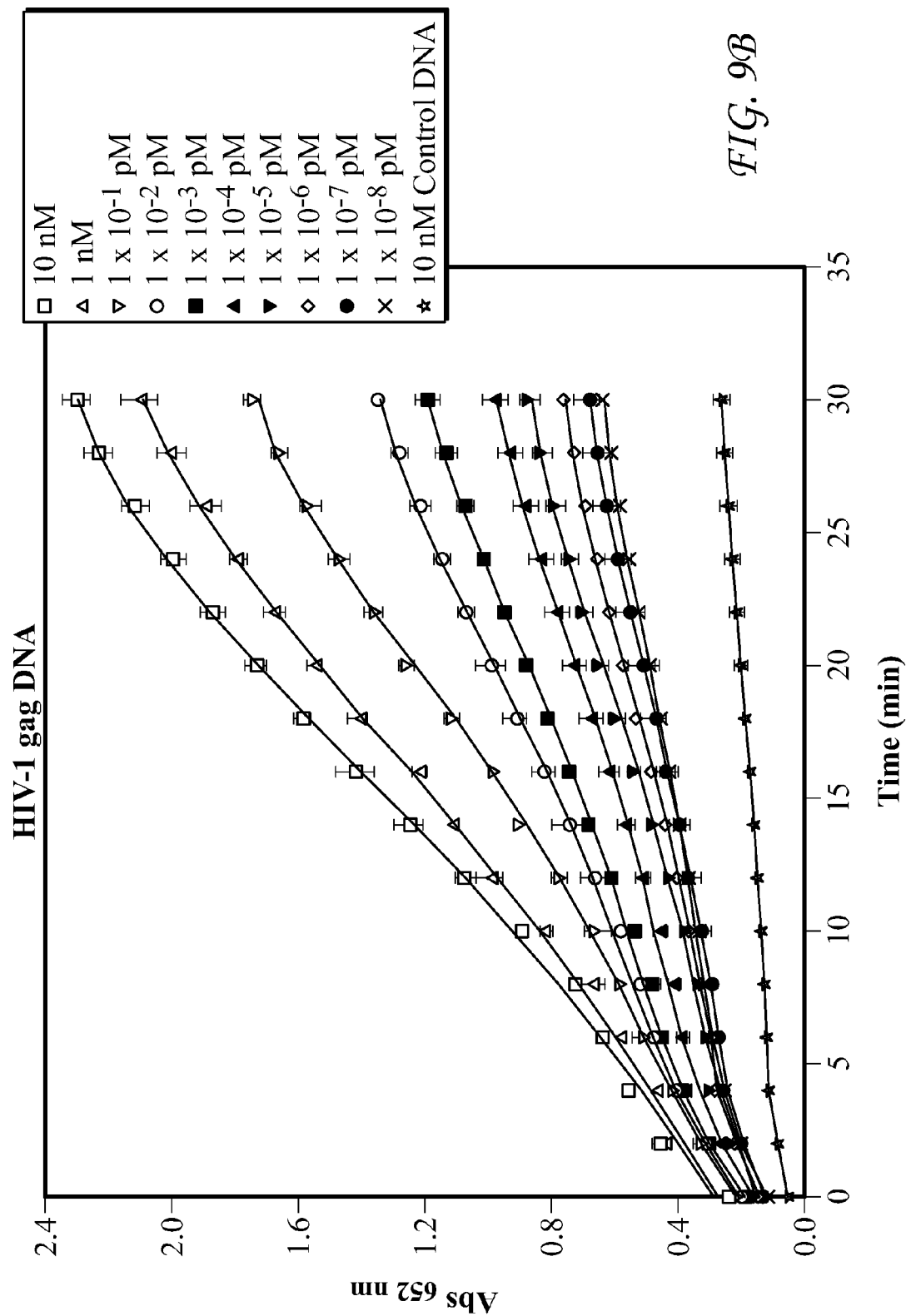
Figure 10A:
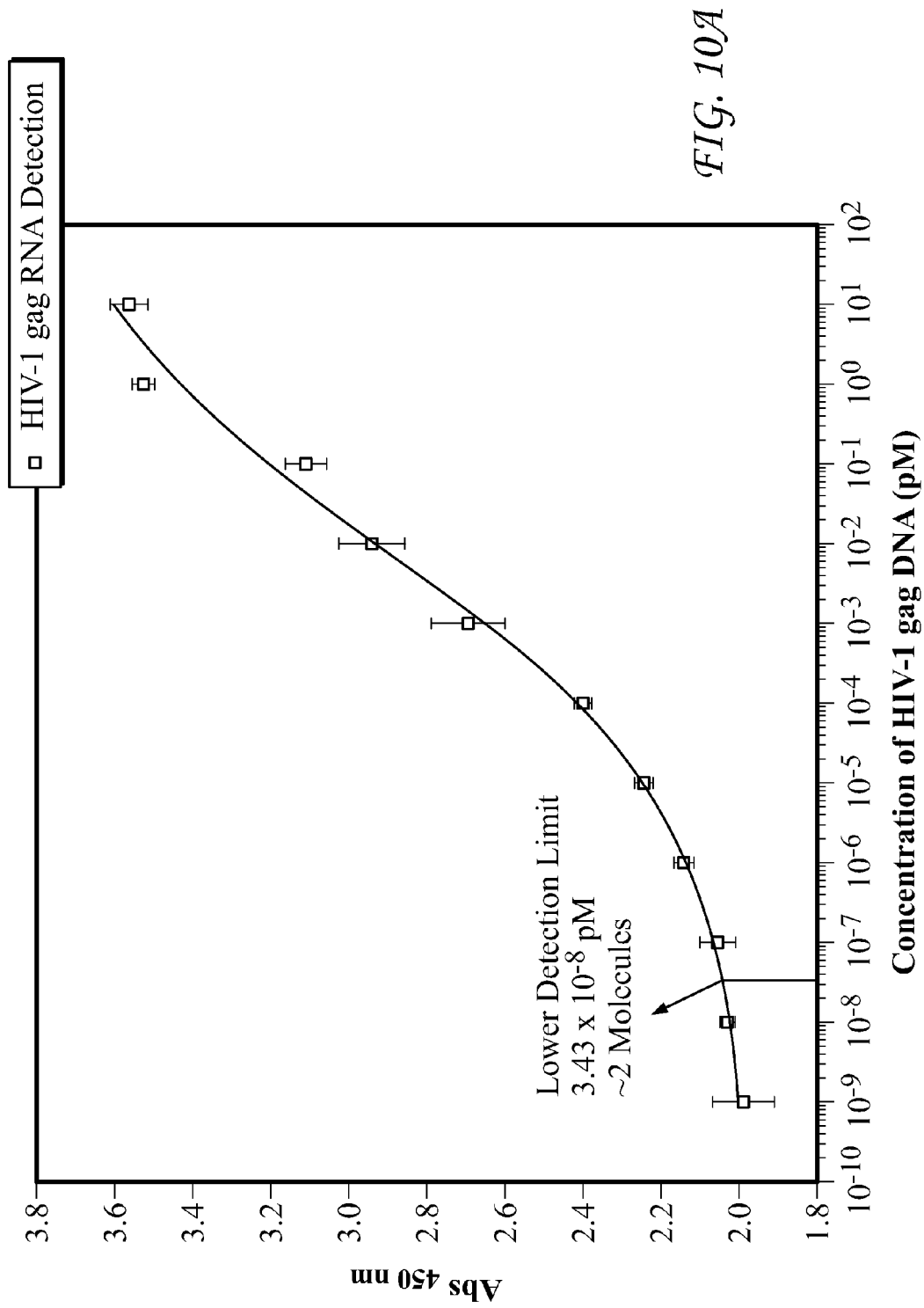
FIG. 10 presents data for HIV-1 gag RNA detection.
Figure 10B:
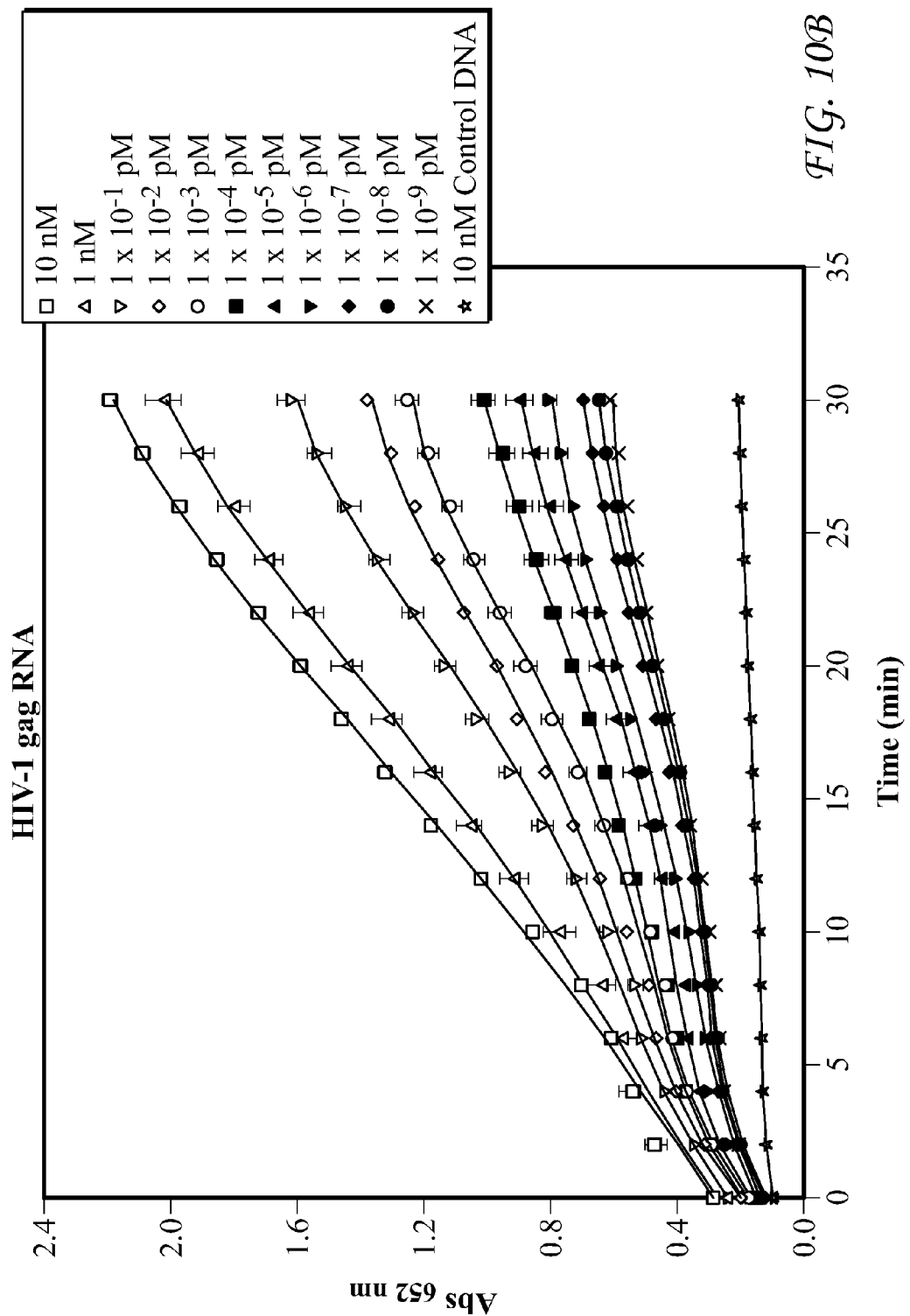
Figure 11A:
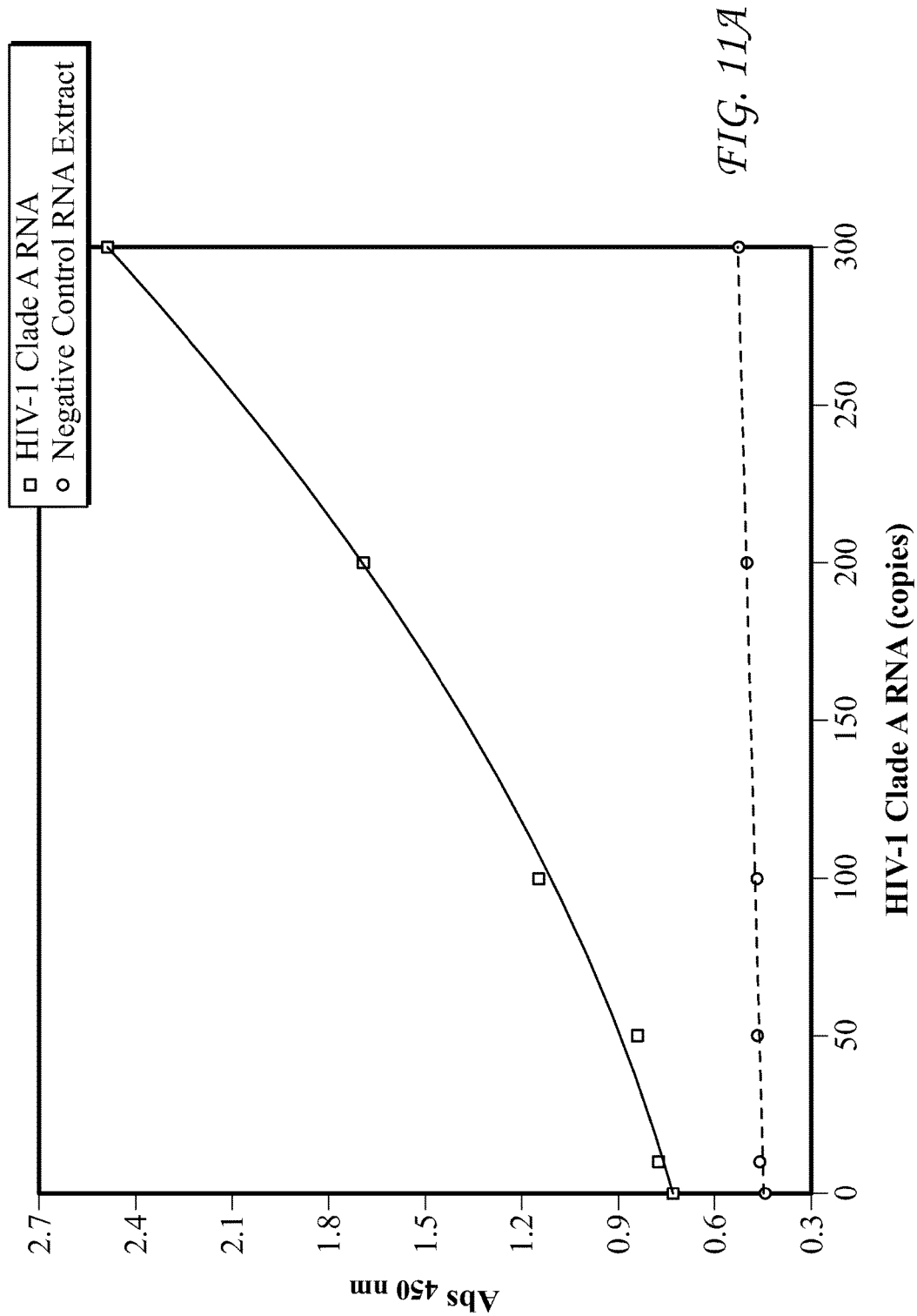
FIG. 11 presents data for HIV-1 Clade A RNA detection
Figure 11B:
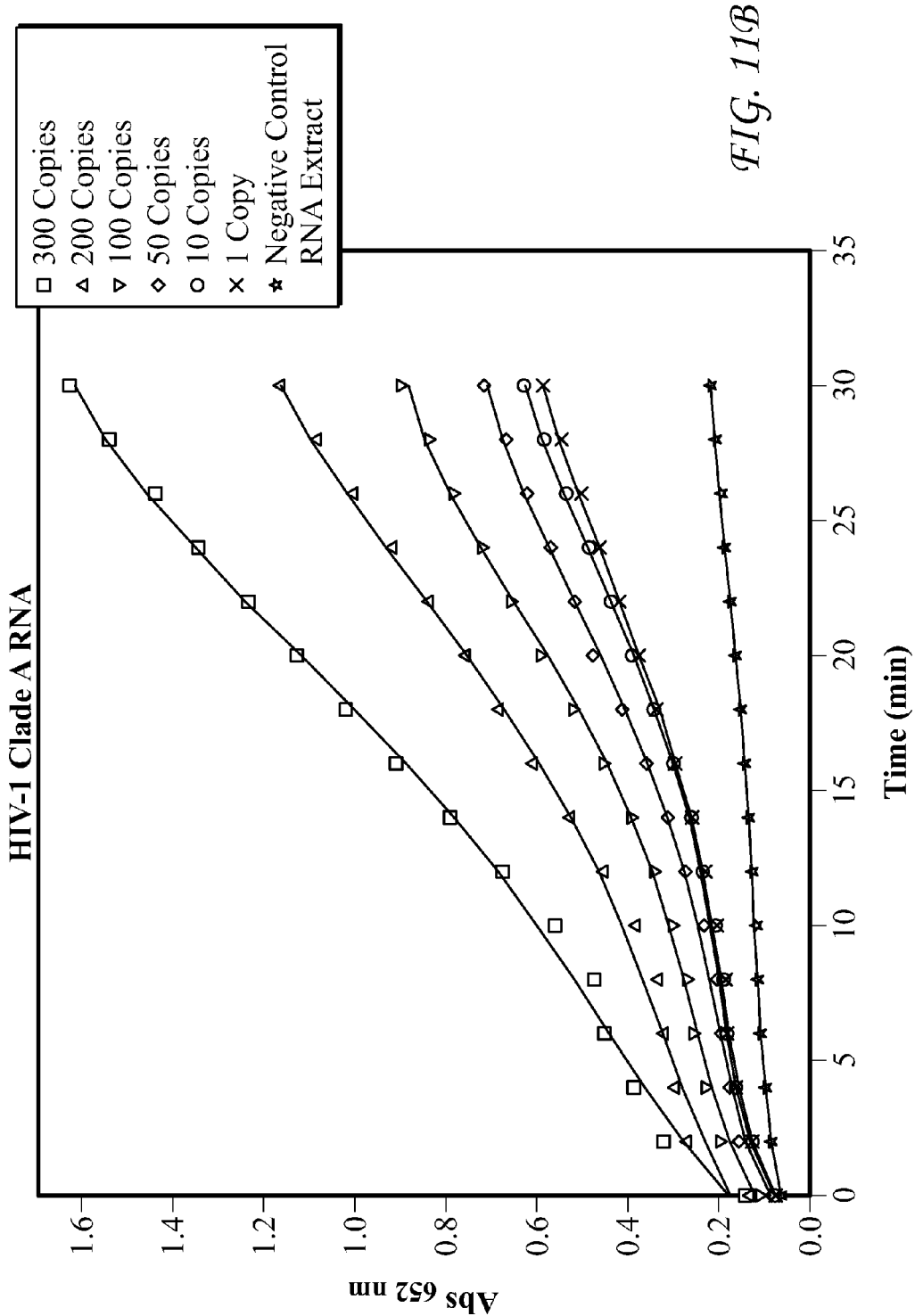
Figure 12A:
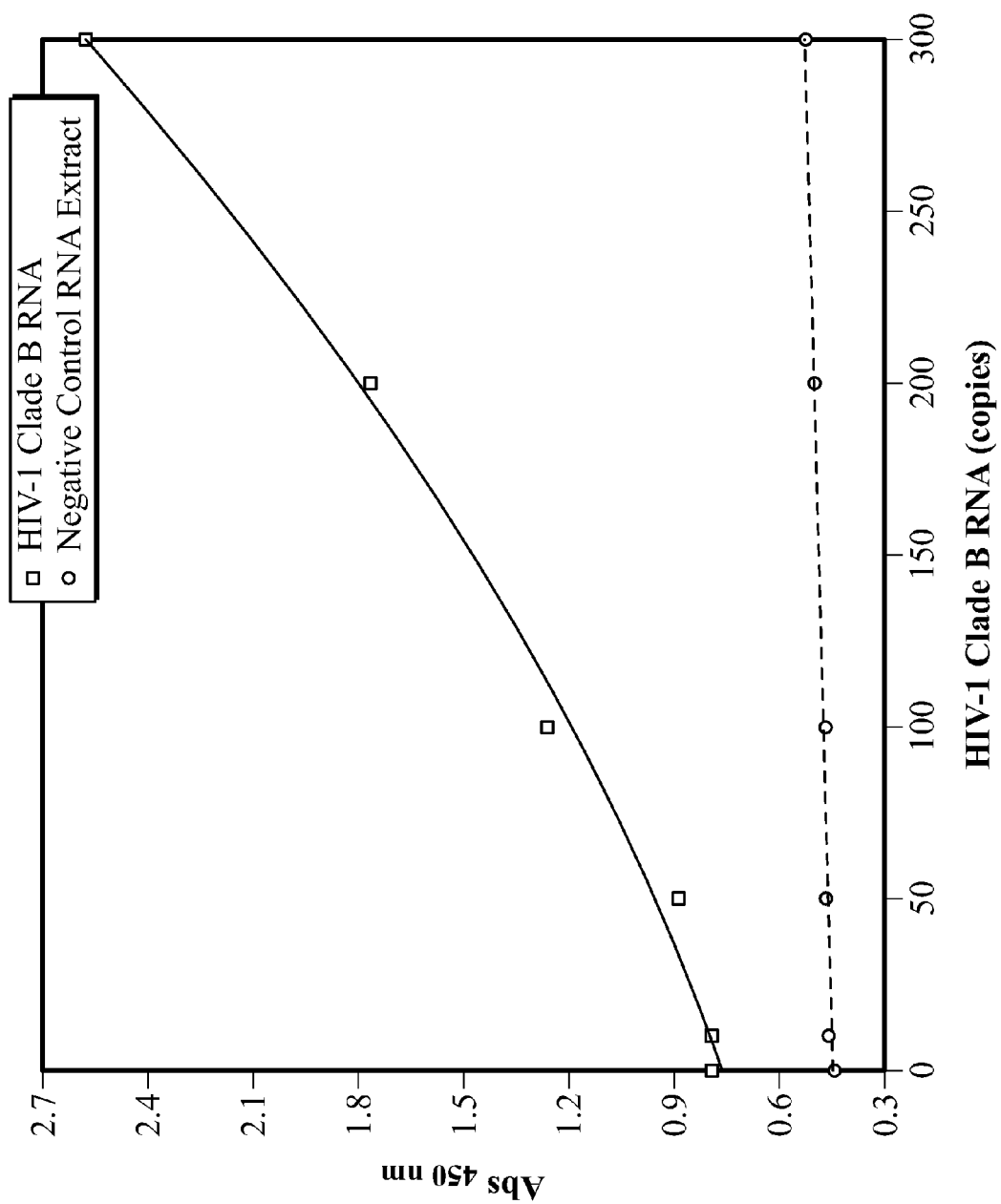
FIG. 12 presents data for HIV-1 Clade B RNA detection.
Figure 12B:
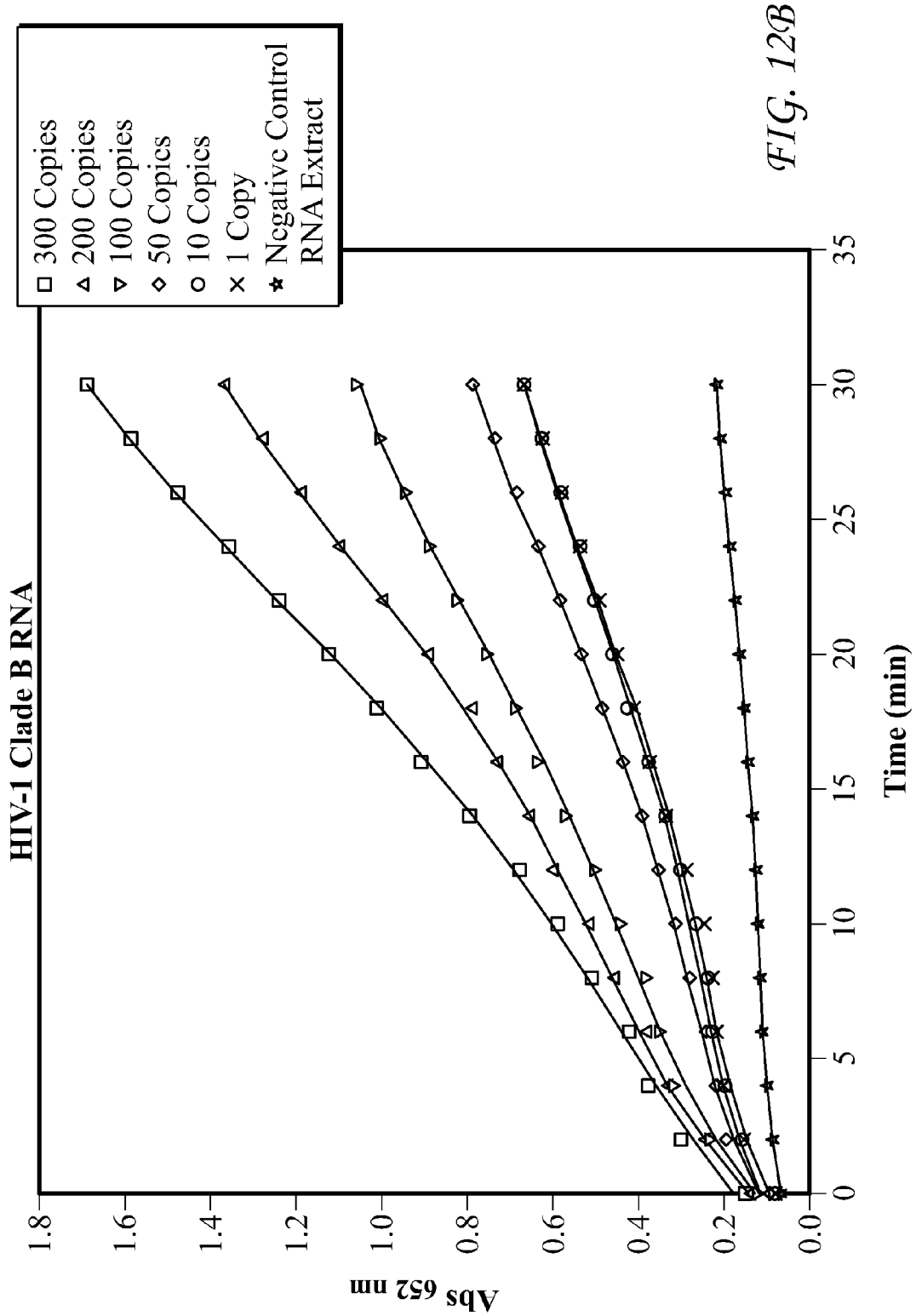
Figure 13A:
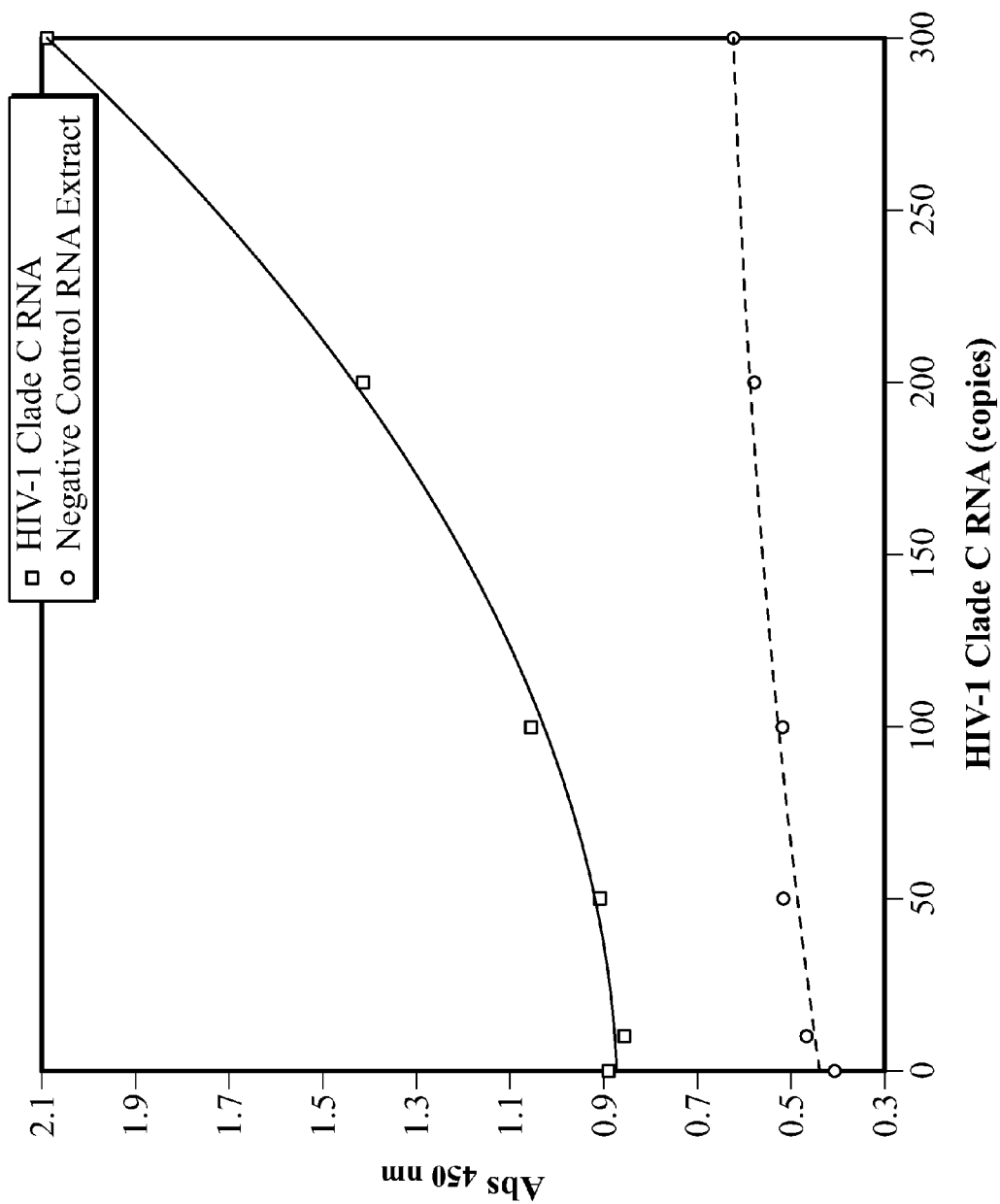
FIG. 13 presents data for HIV-1 Clade C RNA detection.
Figure 13B:
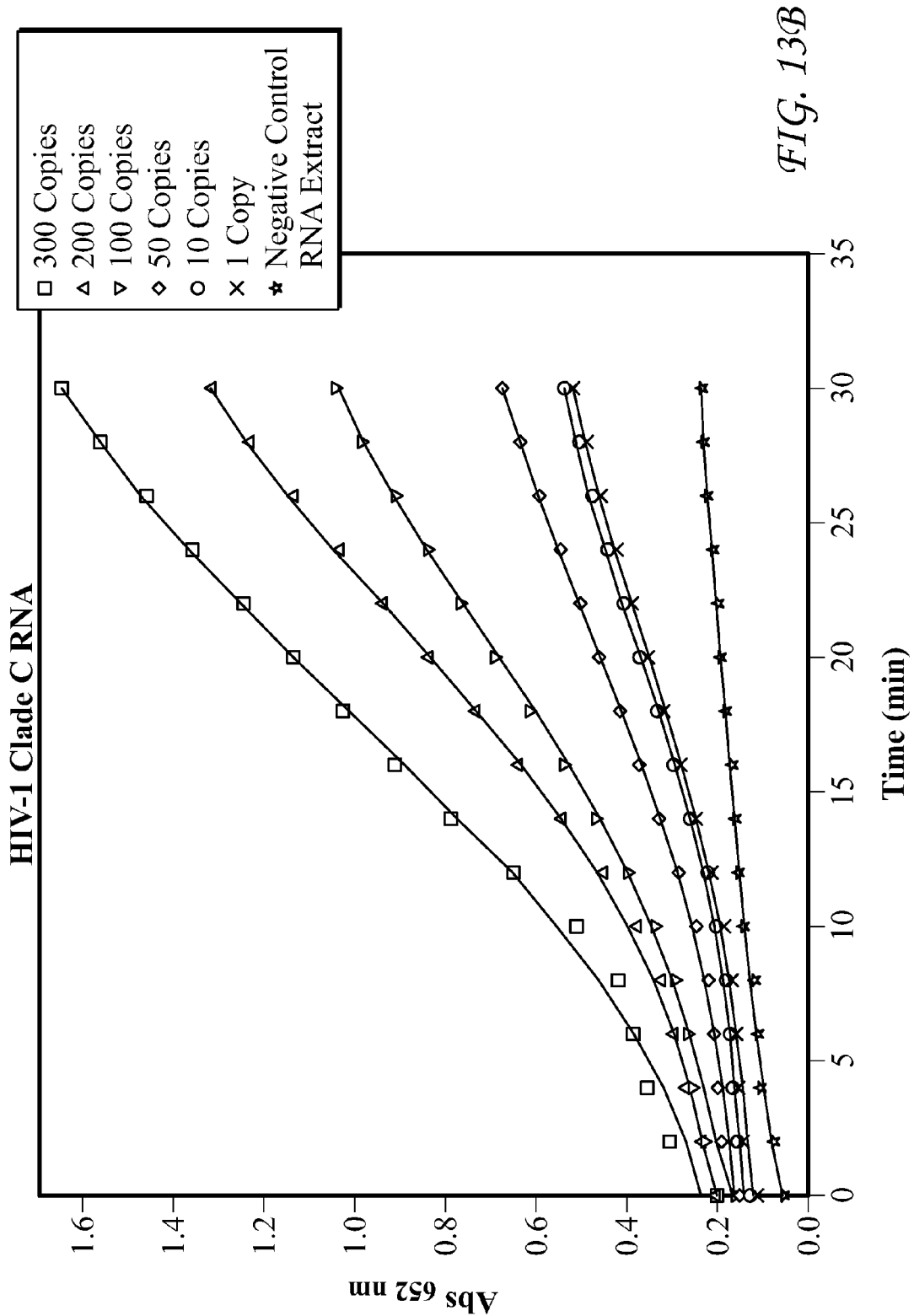
Figure 14A:
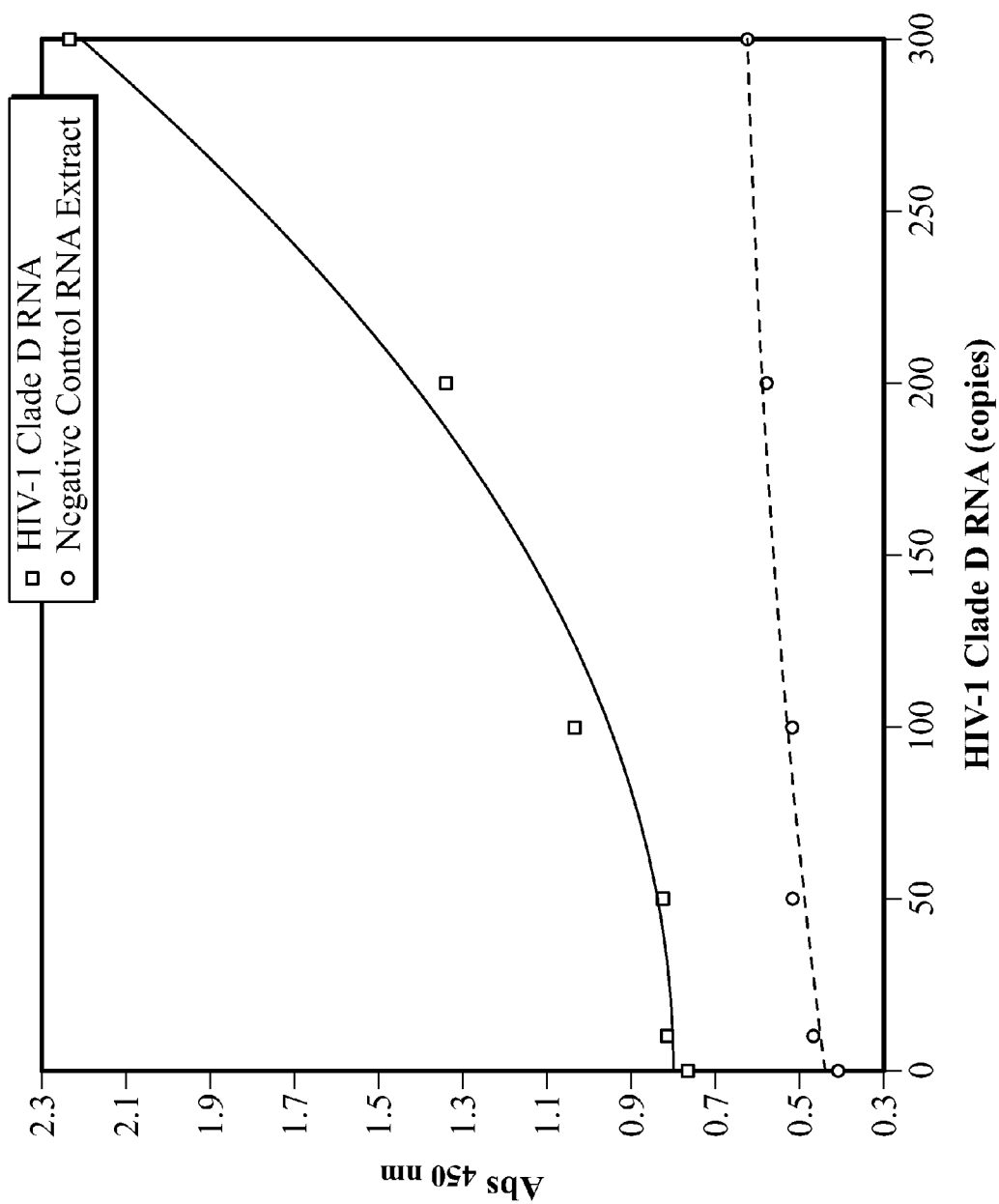
FIG. 14 presents data for HIV-1 Clade D RNA detection.
Figure 14B:
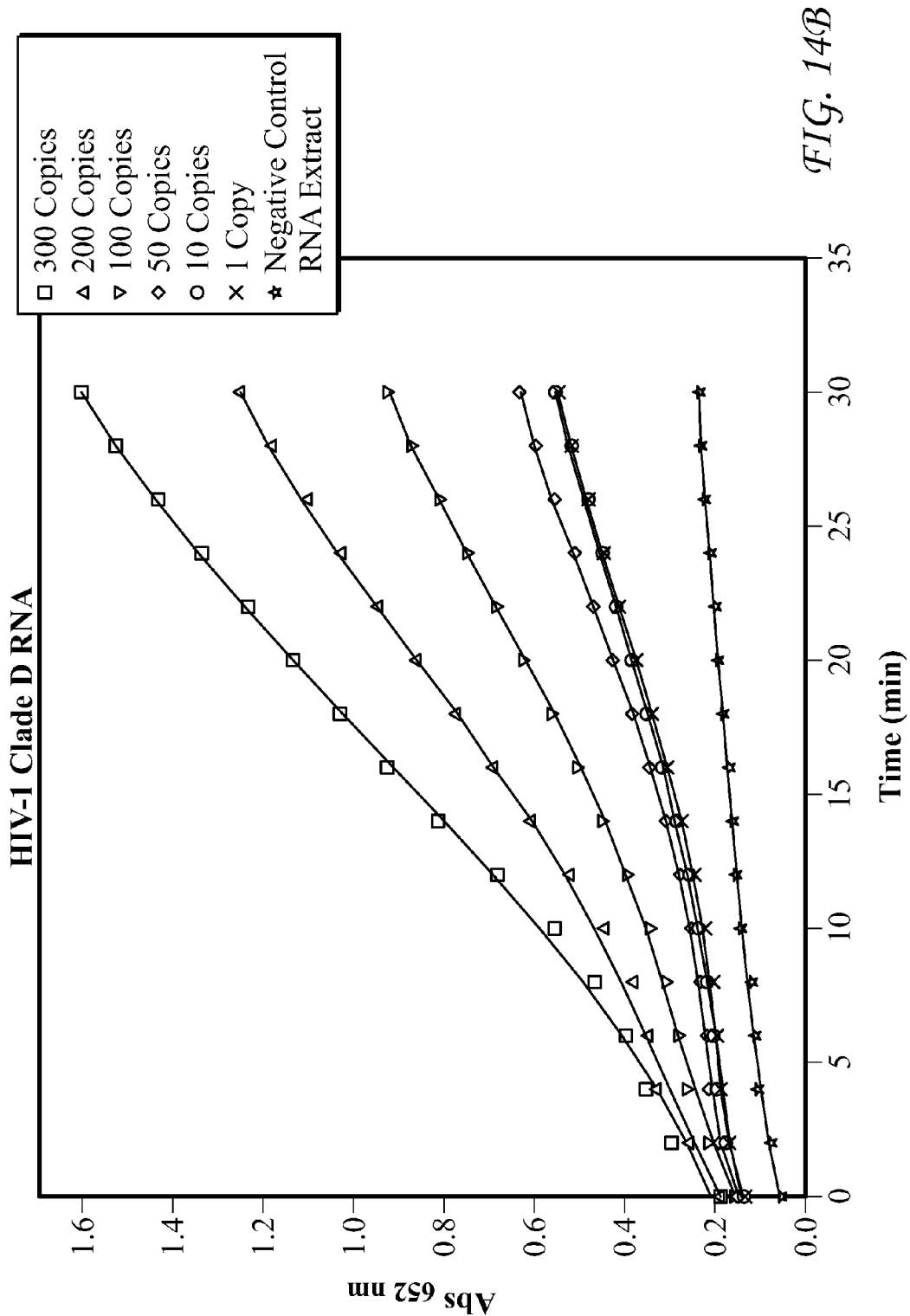
Figure 15A:
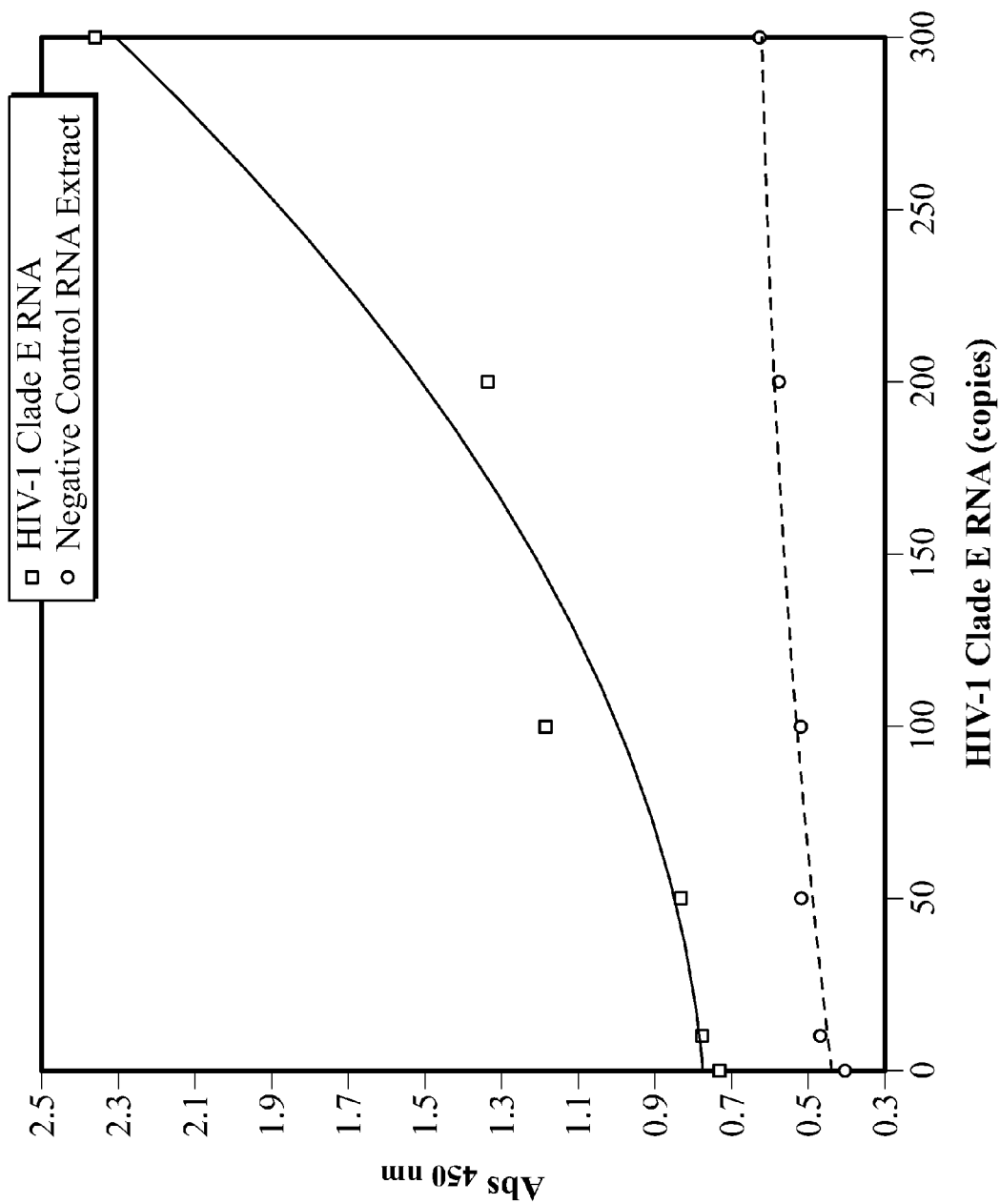
FIG. 15 presents data for HIV-1 Clade E RNA detection.
Figure 15B:
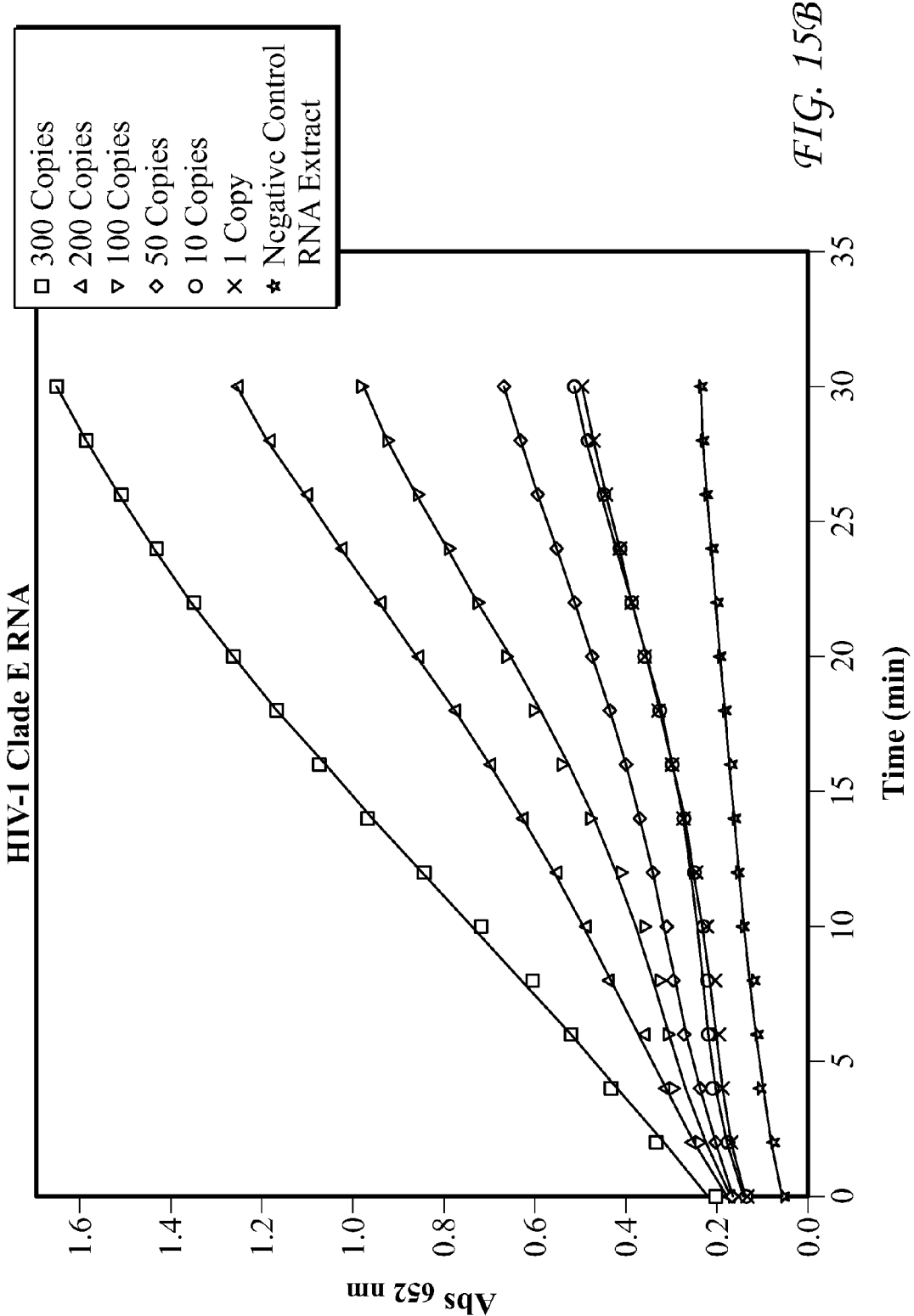
Figure 16A:
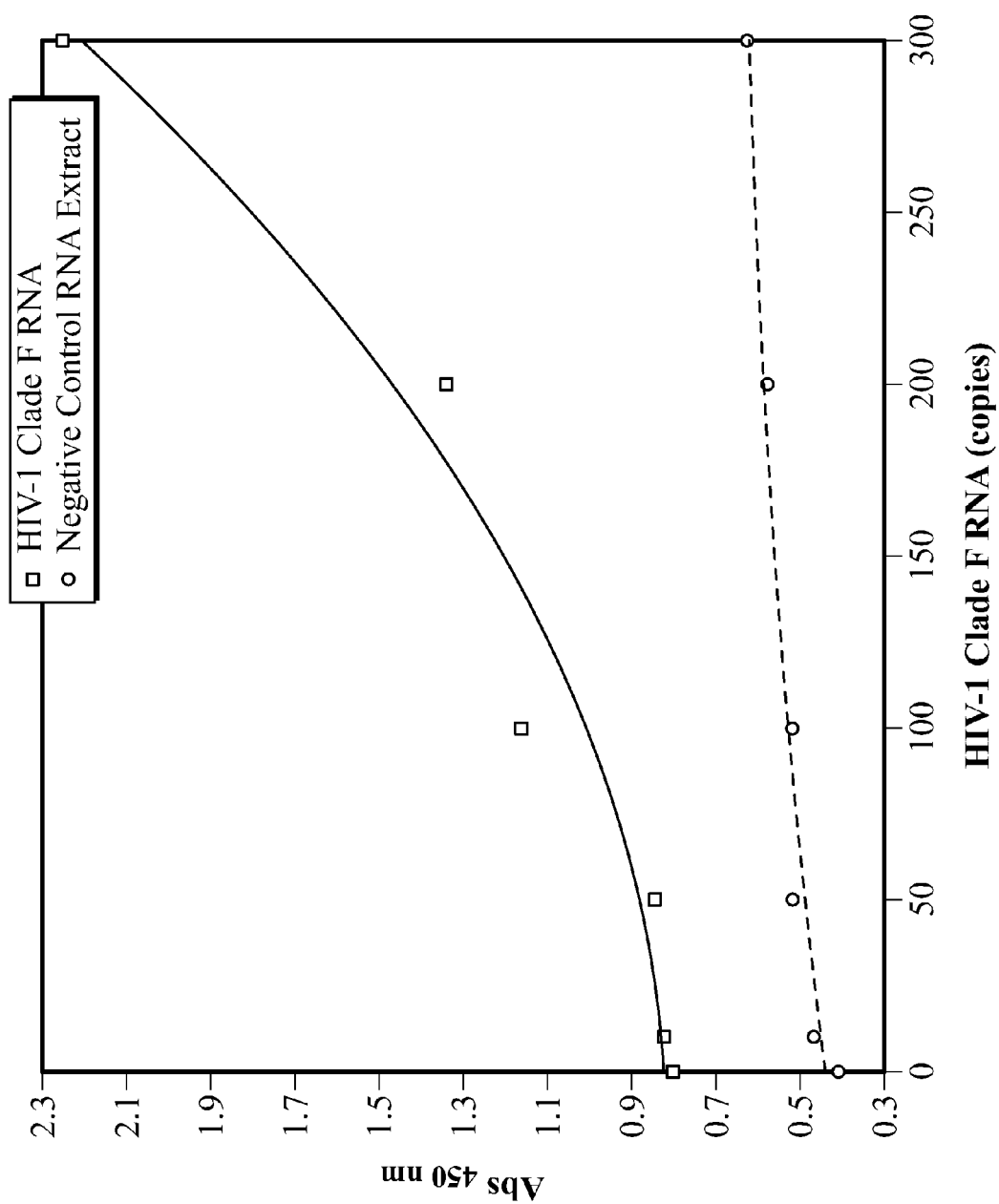
FIG. 16 presents data for HIV-1 Clade F RNA detection.
Figure 16B:
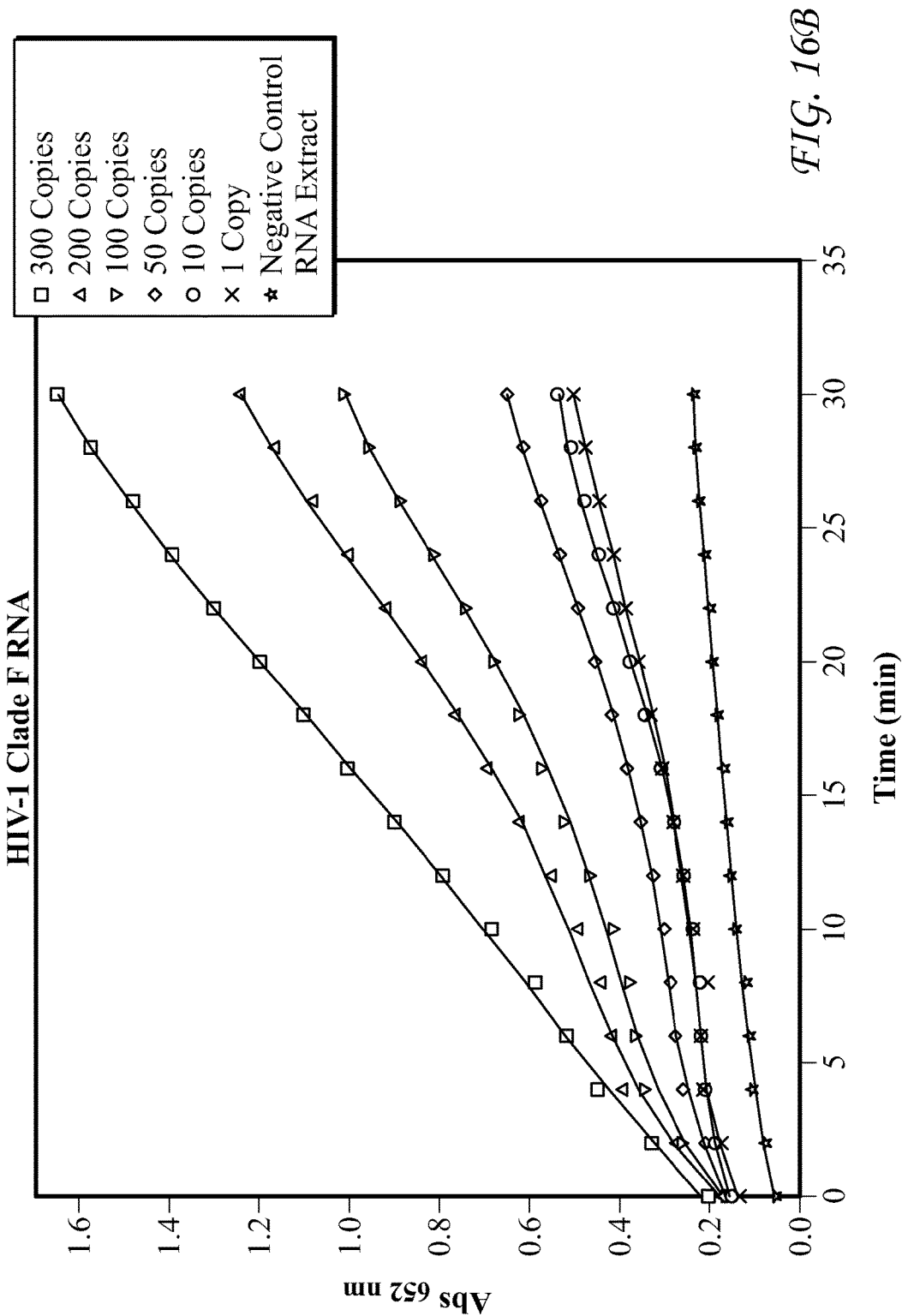
Figure 17A:
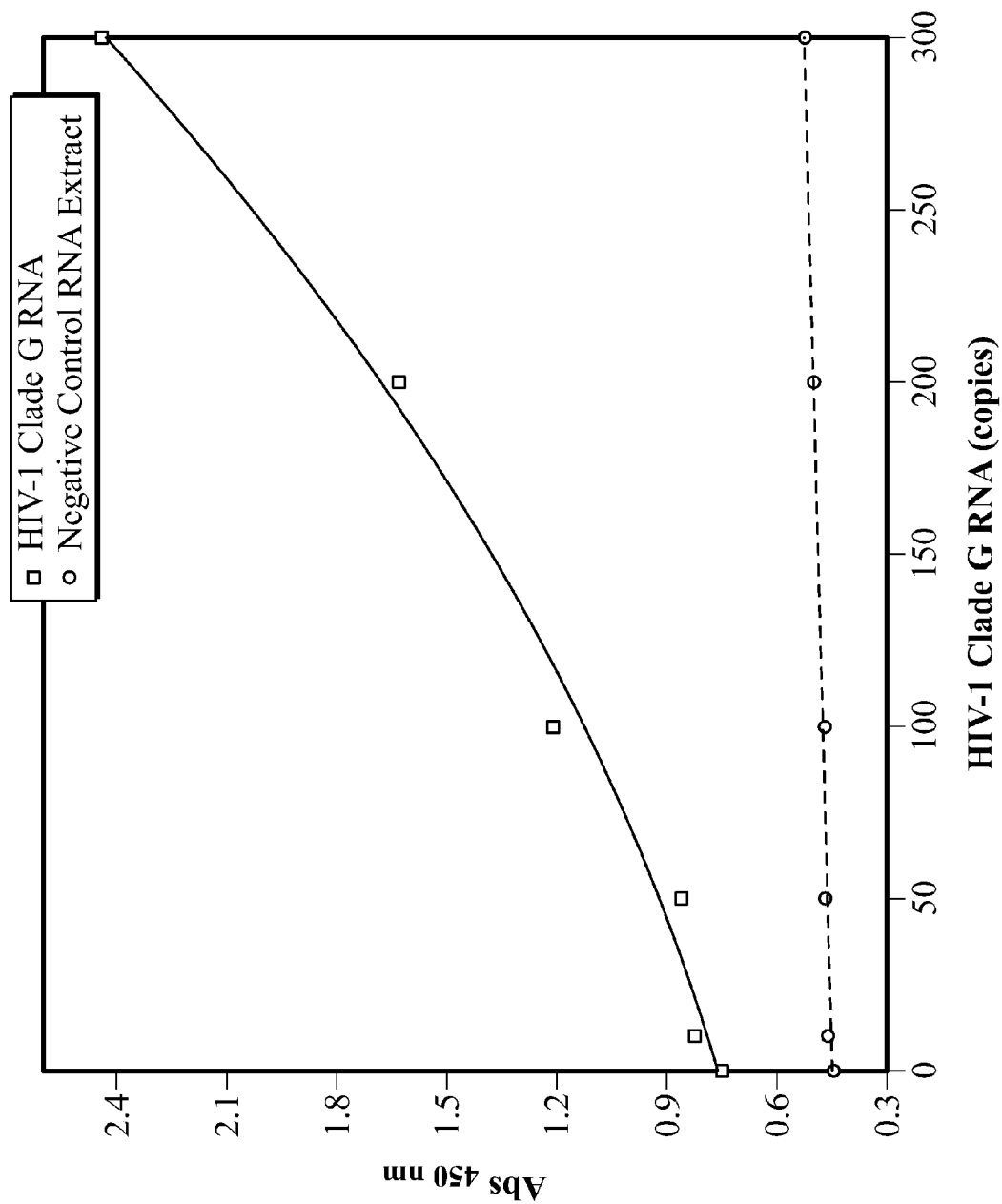
FIG. 17 presents data for HIV-1 Clade G RNA detection.
Figure 17B:
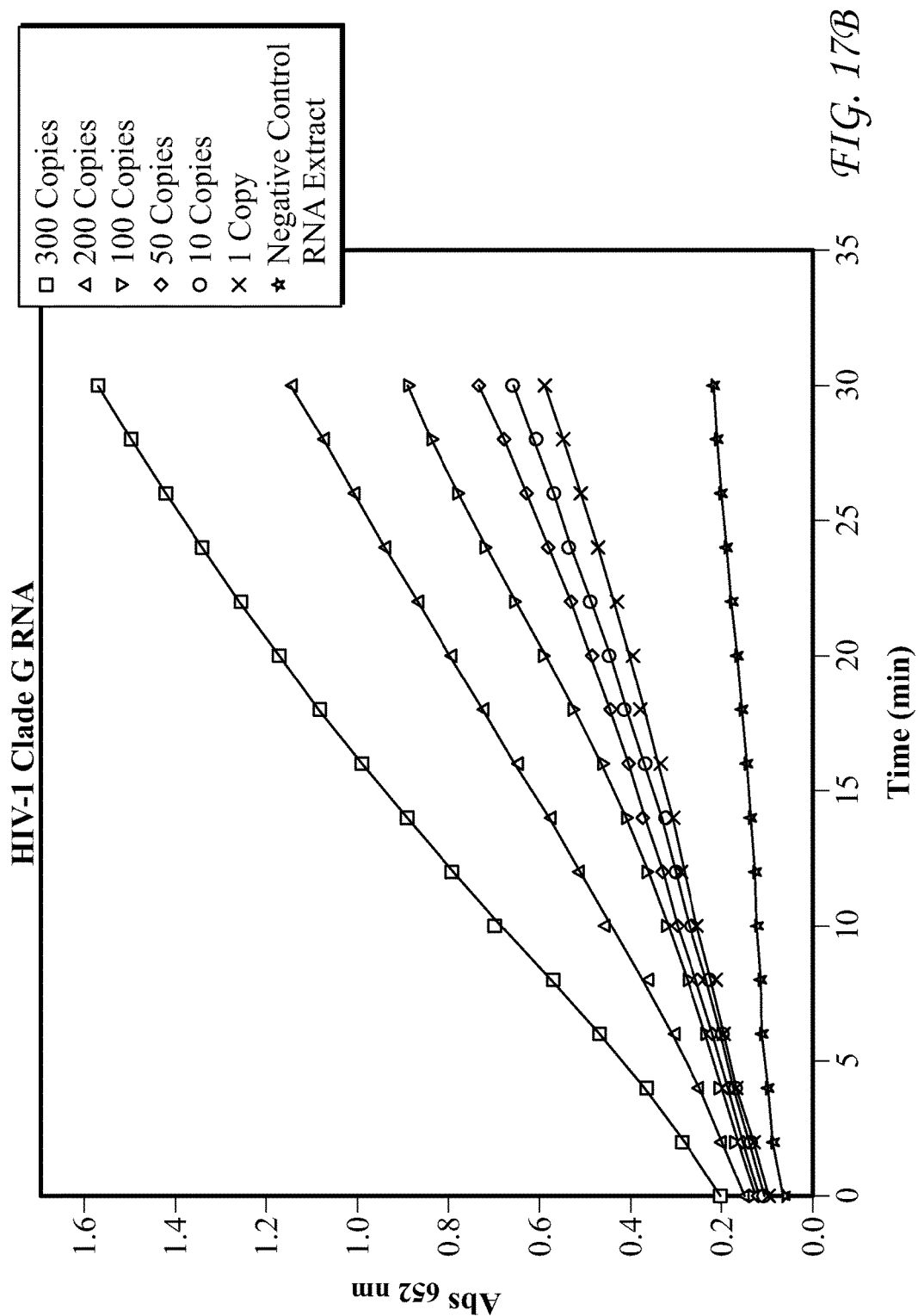
Figure 18A:
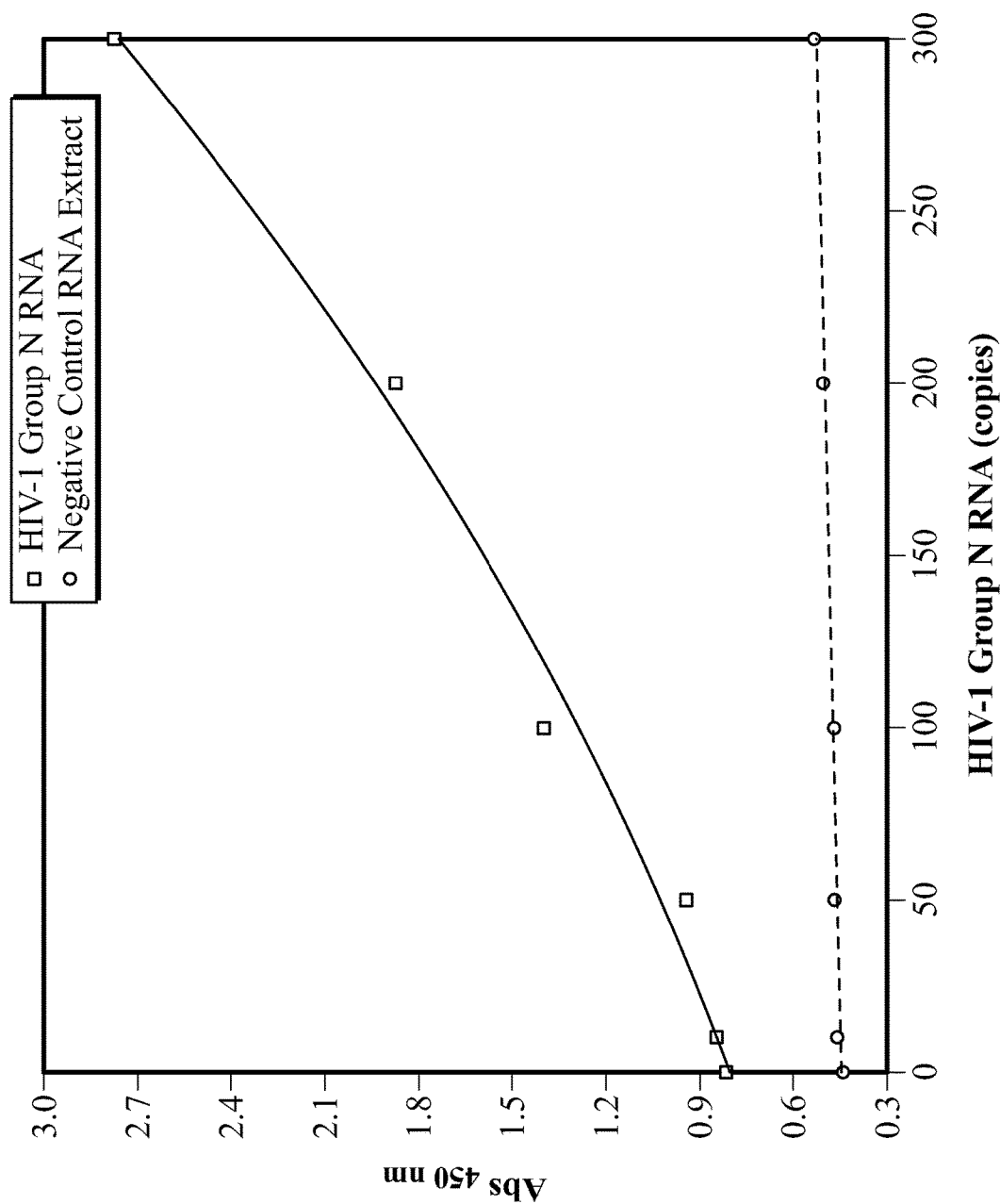
FIG. 18 presents data for Group N RNA detection.
Figure 18B:
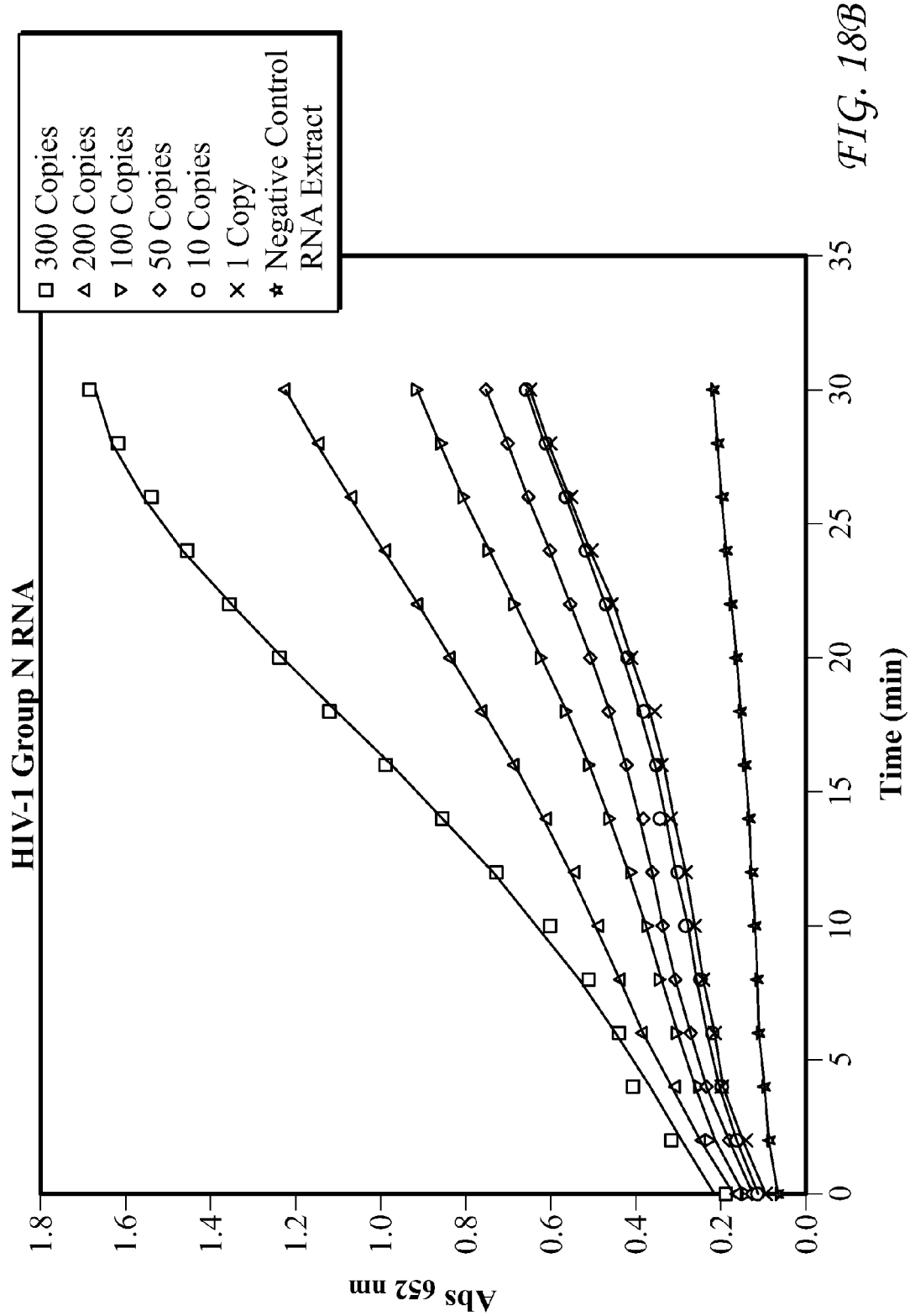
Figure 19A:
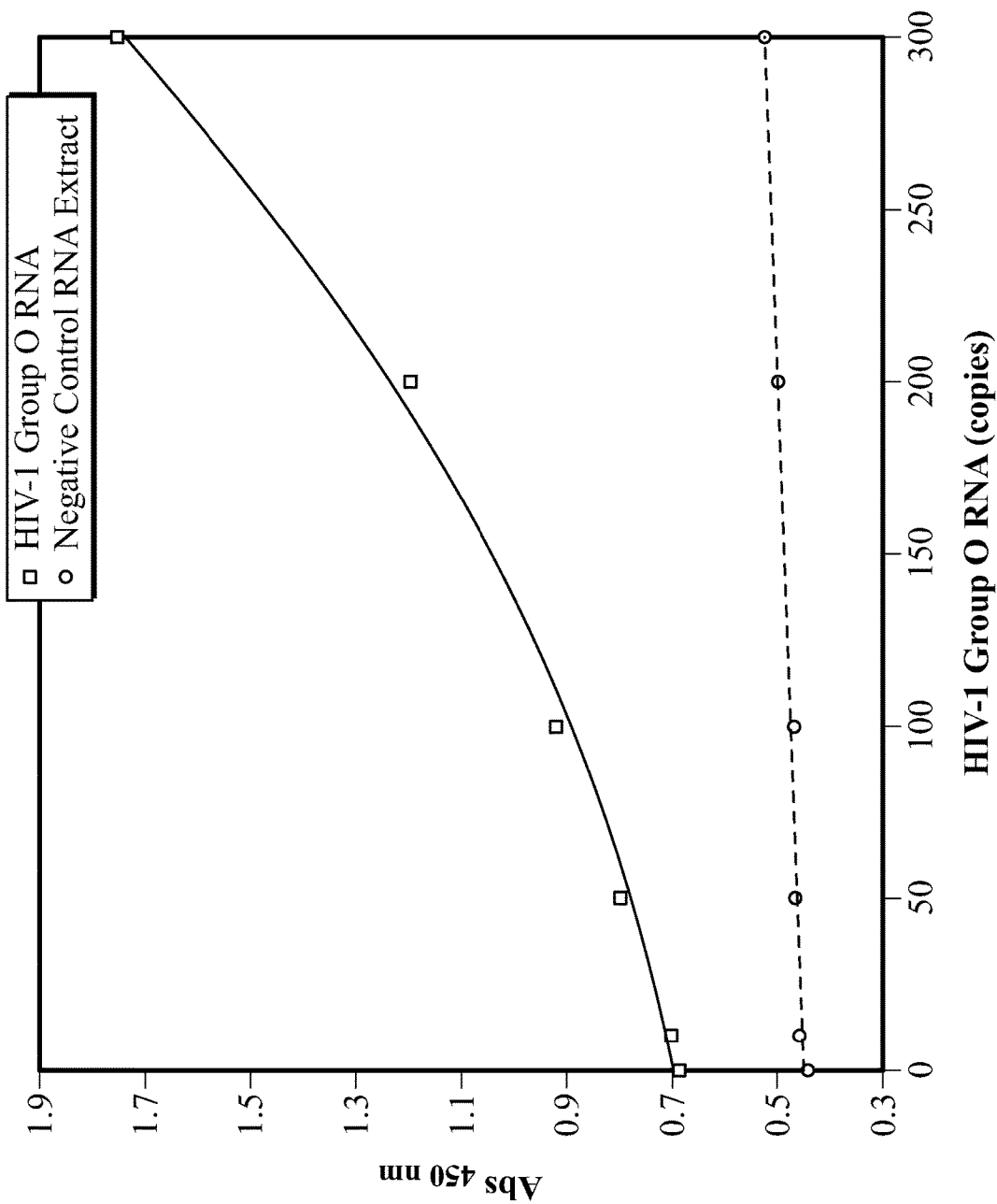
FIG. 19 presents data for Group O RNA detection. In each of FIGS. 9-19, detection results of the target HIV-1 nucleic acids using the SP6/RP6 detection system. (left) Signal response plots (absorbance at 450 nm vs. concentration of HIV-1 nucleic acids) obtained after quenching of enzymatic oxidation with $H_2SO_4$. (right) Time-dependent absorbance changes upon analyzing different concentrations of HIV-1 nucleic acids.
Figure 19B:
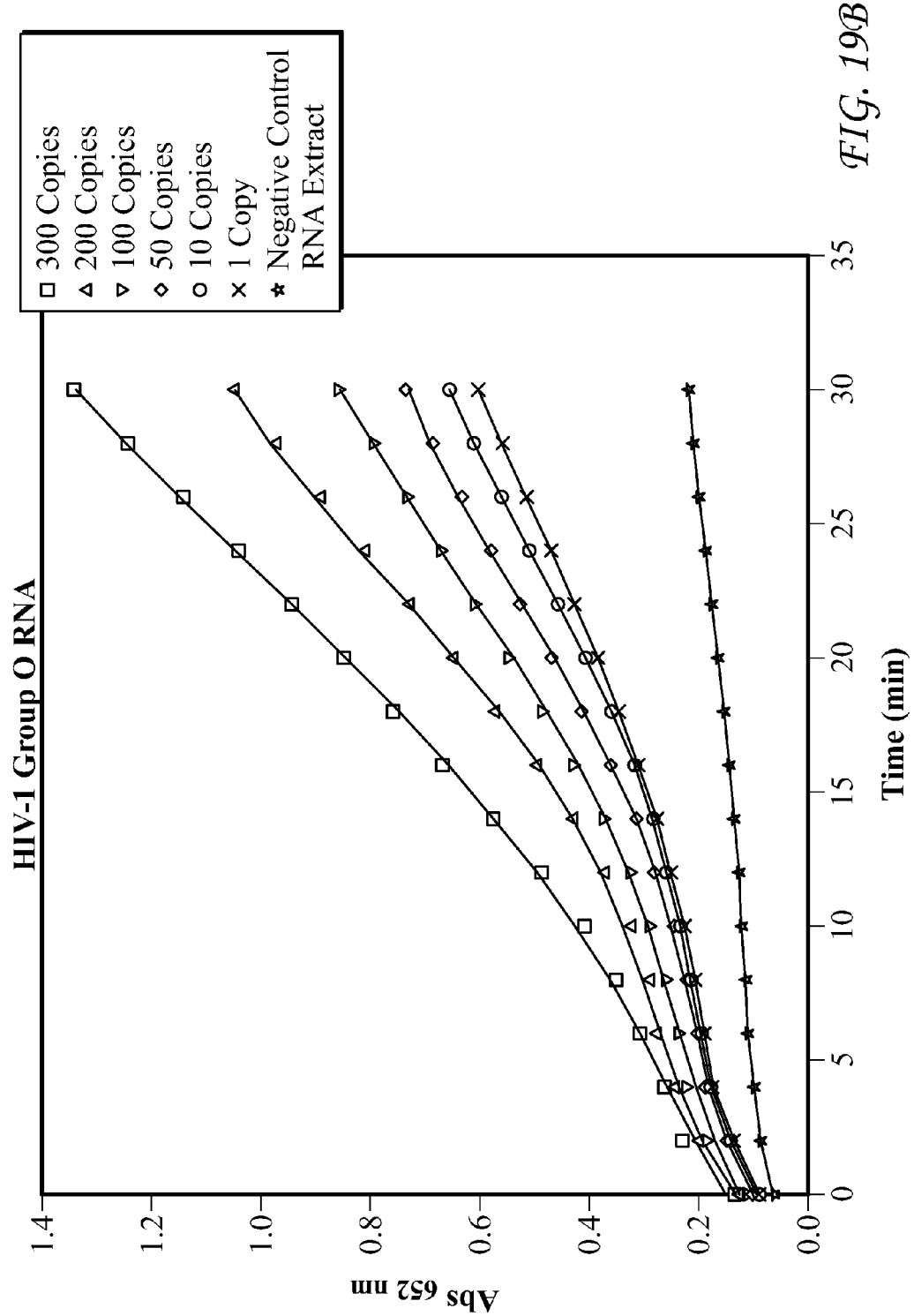

Detection results for RNA and DNA detection are presented in FIGS. 9-19. FIG. 9 presents data for HIV-1 gag DNA detection. FIG. 10 presents data for HIV-1 gag RNA detection. FIG. 11 presents data for HIV-1 Clade A RNA detection. FIG. 12 presents data for HIV-1 Clade B RNA detection. FIG. 13 presents data for HIV-1 Clade C RNA detection. FIG. 14 presents data for HIV-1 Clade D RNA detection. FIG. 15 presents data for HIV-1 Clade E RNA detection. FIG. 16 presents data for HIV-1 Clade F RNA detection. FIG. 17 presents data for HIV-1 Clade G RNA detection. FIG. 18 presents data for Group N RNA detection. FIG. 19 presents data for Group O RNA detection. For FIGS. 9-19, detection results of the target HIV-1 nucleic acids using the SP6/RP6 detection system. (left) Signal response plots (absorbance at 450 nm vs. concentration of HIV-1 nucleic acids) obtained after quenching of enzymatic oxidation with $H_2SO_4$. (right) Time-dependent absorbance changes upon analyzing different concentrations of HIV-1 nucleic acids.

Figure 20:
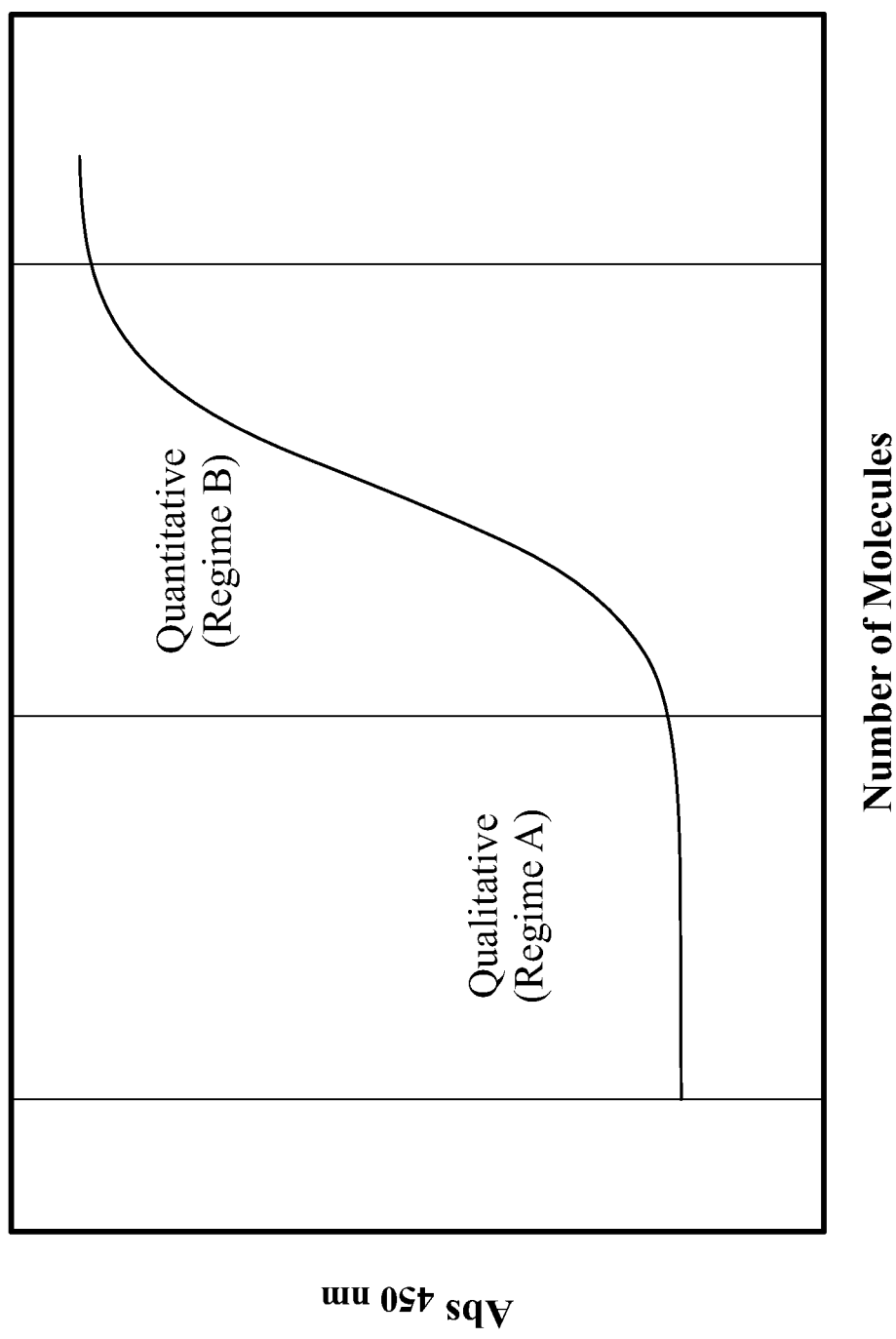
FIG. 20 presents information concerning qualitative versus quantitative detection. In regime A, only the presence but not the amount can be detected. In regime B, the presence and amount can be detected.

FIG. 20 presents information concerning qualitative versus quantitative detection. In regime A, only the presence but not the amount can be detected. In regime B, the presence amount can be detected.

Qualitative and quantitative detection results of HIV-1 nucleic acids by SP6/RP6 detection system are presented in Table 10. Values for quantitative detection are the number of molecules determined from curve fit to absorbance at 450 nm vs. nucleic acids concentration at 90% confidence intervals

TABLE 10

| HIV-1 Nucleic Acids | Lower Limit of Qualitative Detection | Lower Limit of Quantitative Detection |
| --- | --- | --- |
| HIV-1 gag DNA | 1 | 3 |
| HIV-1 gag RNA | 1 | 2 |
| HIV-1 Clade A RNA | 1 | 52 |
| HIV-1 Clade B RNA | 1 | 43 |
| HIV-1 Clade C RNA | 1 | 55 |
| HIV-1 Clade D RNA | 1 | 56 |
| HIV-1 Clade E RNA | 1 | 58 |
| HIV-1 Clade F RNA | 1 | 77 |
| HIV-1 Clade G RNA | 1 | 49 |
| HIV-1 Group N RNA | 1 | 45 |
| HIV-1 Group O RNA | 1 | 50 |

Perspectives

The detection system described herein enables a convenient, colorimetric, long-stable protocol to demonstrate the specificity of the HIV-1 real samples. This protocol eliminates the requirement for a PCR step.

Using PNA probes instead of traditional DNAs can greatly improve the detection devices, and the high thermal stability of PNA-DNA duplexes allows shorter PNA probes to be used compared to DNA. The ability to introduce chemical modifications with predictable effects into the PNA allows us to design PNA probes that impart extraordinarily high sensitivity and selectivity.

These outstanding properties should make this device suitable for early detection of HIV virus. In principle, this assay can also be used to detect any kind of infectious disease by simply changing the PNA sequences of the specific probe.

What is claimed:

1. A method of detecting HIV-1 RNA in a solution obtained from a tissue or blood sample obtained from a human patient, the method comprising
   (a) providing a solution of HIV-1 RNA isolated from the tissue or blood sample,
   (b) contacting the solution with a PNA capture probe and a PNA reporter probe; wherein
      (i) the PNA capture probe comprises at least two trans-cyclopentanes and 15 nucleobases;
      (ii) the PNA reporter probe comprises 6-30 biotin groups and 12 nucleobases, wherein the biotin groups are each attached to the PNA reporter probe via at least one mPEG (8-amino-3,6-dioxaoctanoic acid) linker group;
      (iii) the PNA capture probe is bound to a surface at a N-terminus via covalent binding to form a surface-bound PNA capture probe, wherein the surface is a well of a multiwell plate comprising a polystyrene surface having a surface-attached quinone moiety comprising a (poly)ethyleneglycol-linker-attached electrophilic moiety, wherein the electrophilic moiety is reactive with amino groups; and
      (iv) the PNA capture probe and the PNA reporter probe each comprise a nucleobase sequence that is complementary to different non-overlapping portions of the HIV-1 RNA;
   (d) washing the surface-bound PNA capture probe;
   (e) contacting the surface-bound PNA capture probe with horseradish peroxidase-avidin-conjugate or horseradish peroxidase-streptavidin-conjugate to form a complex;
   (f) contacting the complex with tetramethylbenzidine and peroxide; and (g) determining an emergence of an absorbance of visible light at a wavelength of 652 nm spectrometrically or determining an appearance of a blue color by visual observation, wherein the emergence of absorbance or the appearance of the blue color indicates the presence of a complex formed from the surface-bound PNA capture probe, the PNA reporter probe, the horseradish peroxidase-avidin-conjugate or horseradish peroxidase-streptavidin-conjugate, and the HIV-1 RNA, wherein the emergence of the absorbance of visible light at a wavelength of 652 nm or appearance of the blue color arises from oxidation of tetramethylbenzidine by horseradish peroxidase-avidin-conjugate or horseradish peroxidase-streptavidin-conjugate present in the complex;

wherein the presence of the HIV-1 RNA in the tissue or blood sample permits the detection of HIV in the patient, wherein the HIV-1 RNA is detected when 5 to 100 copies of the HIV-1 RNA are present in the solution being tested.

2. The method of claim 1, wherein the surface is visually observed to detect the appearance of visible light from the reporter probe.

3. The method of claim 1, wherein the PNA reporter probe biotin groups are bound to horseradish peroxidase-avidin-conjugate or horseradish peroxidase-streptavidin-conjugate.

4. The method of claim 1, wherein the PNA capture probe comprises at least three trans-cyclopentanes.

5. The method of claim 1, wherein the HIV-1 RNA is HIV gag.

6. The method of claim 1, further comprising a step (f') after step (f) of contacting the complex with $H_2SO_4$, and a step (g') after step (f') in place of step (g) of determining an emergence of an absorbance of visible light at a wavelength of 450 nm spectrometrically or determining an appearance of a yellow color by visual observation, wherein the emergence of absorbance or appearance of the yellow color indicates the presence of a complex formed from the PNA capture probe, the PNA reporter probe, the horseradish peroxidase avidin conjugate or horseradish peroxidase streptavidin-conjugate, and the HIV-1 RNA, bound to the surface, wherein the emergence of the absorbance of visible light at a wavelength of 450 nm or appearance of the yellow color arises from quenching of the oxidation of tetramethylbenzidine by horseradish peroxidase-avidin-conjugate or horseradish peroxidase-streptavidin-conjugate present in the complex.

7. A kit for detecting HIV-1 RNA present in a solution obtained from a tissue or blood sample obtained from a human patient, the kit comprising:

a PNA capture probe comprising at least two trans-cyclopentanes, wherein the PNA capture probe comprises 15 nucleobases; the PNA capture probe being bound to a surface at a N-terminus via covalent binding, wherein the surface is a well of a multiwell plate comprising a polystyrene surface having a surface-attached quinone moiety comprising a (poly)ethyleneglycol-linker-attached electrophilic moiety, wherein the electrophilic moiety is reactive with amino groups;

a PNA reporter probe comprising 6-30 biotin groups, wherein the PNA reporter probe comprises 12 nucleobases, wherein the biotin groups are each attached to the PNA reporter probe via at least one mPEG (8-amino-3,6-dioxaoctanoic acid) linker group; and horseradish peroxidase-avidin-conjugate or horseradish peroxidase-streptavidin-conjugate;

wherein the PNA capture probe and the PNA reporter probe each comprise a sequence that is complementary to different non-overlapping portions of HIV-1 RNA.

8. The kit of claim 7, wherein the PNA capture probe comprises at least three trans-cyclopentanes.

\* \* \* \* \*